US008069420B2

(12) United States Patent
Plummer

(10) Patent No.: US 8,069,420 B2
(45) Date of Patent: Nov. 29, 2011

(54) SYSTEM FOR CONTROLLING THE COMMUNICATION OF MEDICAL IMAGING DATA

(75) Inventor: Roderick Plummer, Corona, CA (US)

(73) Assignee: Karl Storz Endoscopy-America, Inc., Culver City, CA (US)

( * ) Notice: Subject to any disclaimer, the term of this patent is extended or adjusted under 35 U.S.C. 154(b) by 1162 days.

(21) Appl. No.: 11/025,715

(22) Filed: Dec. 29, 2004

(65) Prior Publication Data

US 2006/0152516 A1    Jul. 13, 2006

(51) Int. Cl.
*G06F 3/048* (2006.01)
(52) U.S. Cl. ......... 715/835; 715/771; 715/839; 600/921
(58) Field of Classification Search ............... 715/500.1, 715/716, 810, 771, 835, 839; 600/921
See application file for complete search history.

(56) References Cited

U.S. PATENT DOCUMENTS

| | | | | |
|---|---|---|---|---|
| 6,638,223 | B2 | 10/2003 | Lifshitz et al. ................ | 600/440 |
| 2002/0060302 | A1* | 5/2002 | Aonuma ........................ | 250/583 |
| 2003/0036687 | A1* | 2/2003 | Schoenberg et al. ......... | 600/301 |
| 2003/0093503 | A1* | 5/2003 | Yamaki et al. ................ | 709/220 |
| 2003/0146942 | A1 | 8/2003 | Helgason et al. ............. | 345/968 |
| 2003/0171740 | A1 | 9/2003 | Stiller et al. .................. | 606/1 |
| 2004/0023198 | A1 | 2/2004 | Youngman .................... | 434/262 |
| 2004/0024384 | A1 | 2/2004 | Novak .............................. | 606/1 |
| 2004/0138569 | A1 | 7/2004 | Grunwald et al. ............ | 600/459 |
| 2004/0169673 | A1* | 9/2004 | Crampe et al. ................ | 345/700 |
| 2005/0097191 | A1* | 5/2005 | Yamaki et al. ................ | 709/219 |
| 2005/0125256 | A1* | 6/2005 | Schoenberg et al. ............ | 705/2 |
| 2006/0041181 | A1* | 2/2006 | Viswanathan et al. ......... | 600/11 |
| 2006/0052676 | A1* | 3/2006 | Wang et al. ................... | 600/300 |
| 2006/0149601 | A1* | 7/2006 | Langhofer et al. ............... | 705/3 |
| 2007/0094197 | A1* | 4/2007 | Datena et al. .................. | 706/46 |

* cited by examiner

*Primary Examiner* — Namitha Pillai
(74) *Attorney, Agent, or Firm* — St. Onge Steward Johnston & Reens LLC

(57) ABSTRACT

A system for controlling the communication of medical imaging data is disclosed generally comprising a computer, a plurality of sources of medical imaging data and a plurality of destinations of medical imaging data in communication with the computer, and a touchscreen for simultaneously displaying a plurality of source icons and a plurality of destination icons controlled by the computer. The source icons correspond to the plurality of sources to allow a user to select a particular source of imaging data, and the destination icons correspond to the plurality of destinations to allow the user to select at least one particular destination for the imaging data. In certain embodiments, the touchscreen includes a display window for displaying medical images generated from the imaging data supplied by the presently selected source. In some embodiments, the touchscreen includes a set of controls associated with the presently selected source.

84 Claims, 24 Drawing Sheets

SYSTEM FOR CONTROLLING THE COMMUNICATION OF MEDICAL IMAGING DATA

FIELD OF THE INVENTION

The present invention relates to a system for controlling the communication of medical imaging data. More specifically, the invention relates to a touchscreen interface for routing and controlling medical imaging data between a number of different sources and destinations.

BACKGROUND OF THE INVENTION

Today, a wide variety of medical imaging systems are known for performing diagnostic and surgical procedures. Specifically, systems have been developed to increase a surgeon's ability to perform surgery on a patient by providing the surgeon with intra-operative images of anatomical structures within a patient's body. Accordingly, during various types of minimally invasive surgeries—such as endoscopic, arthroscopic, and laparoscopic procedures—a surgeon is able to visually examine the interior of an organ or joint while the surgeon is conducting the surgery.

These systems typically include the use of some specialized form of camera or medical endoscope. Additionally, recent developments have resulted in systems incorporating various audiovisual devices to allow both the surgeon, as well as others in the surgical suite or located remotely therefrom who may be assisting or observing, to better monitor the procedure. Accordingly, both still images and live video being acquired during the surgery can be output to various different screens or recording devices. Additionally, various devices have been incorporated into these systems to allow the surgeon, or other individuals assisting or observing, to utilize the imaging capabilities of the system in different ways, simultaneously or at different times, for a variety of different objectives.

For example, a surgeon may wish to view a live video feed, and freeze and capture images as he does so, and then compare those frozen images with other images of the same patient that were stored during a previous procedure. As another example, a doctor may wish to record a clean copy of video on a linear tape deck, yet also annotate or telestrate on that video and then digitally record this marked video as well. As yet another example, an observer may wish to view the surgical suite and the doctor's movements, while simultaneously viewing the results of those movements taking place inside the patient's body.

In light of the many capabilities that have emerged with respect to medical imaging, and the many devices (and interconnection of those devices) necessary to realize those capabilities, many surgical suites have become fairly complex just with respect to the imaging aspect of the procedure alone. Though certain systems presently exist for centrally controlling various medical devices in an operating room, there is presently a need to provide a way of interfacing with all of the imaging devices available for the procedure that is simpler to use and permits quicker execution than present systems for controlling devices, which may entail detailed command inputs, such as by a keyboard, or hierarchies of menus and sub-menus.

As a result, there is a need to provide users with a system for interfacing with many imaging devices potentially useful in a medical procedure that allows the user to easily and quickly select particular devices and route imaging data from various devices to various other devices. Additionally, there is a need to allow the user to easily control the devices that are presently selected. Finally, there is a need to allow a user to easily preview or alter the images that are being routed to the other individuals to whom the images are ultimately being communicated.

What is desired, therefore, is a system for controlling the communication of medical imaging data that allows a user to easily and quickly select sources of imaging data. What is further desired is a system for controlling the communication of medical imaging data that allows a user to easily and quickly select particular destinations for the medical imaging data. What is also desired is a system that allows a user to view the medical imaging data presently being routed. What is further desired is a system that allows a user to easily control the sources of the imaging data.

SUMMARY OF THE INVENTION

Accordingly, it is an object of the present invention to provide a system for controlling the communication of medical imaging data that enables the user to immediately view the available sources of medical imaging data and select a particular source therefrom without engaging in any preliminary activity.

It is a further object of the present invention to provide a system for controlling the communication of medical imaging data that enables the user to immediately view the available destinations of medical imaging data and select particular destinations therefrom without engaging in any preliminary activity.

It is yet another object of the present invention to provide a system for controlling the communication of medical imaging data that enables the user to view medical images generated from medical imaging data from a presently selected source without engaging in any preliminary activity.

It is still another object of the present invention to provide a system for controlling the communication of medical imaging data that enables the user to control a presently selected source of medical imaging data without engaging in any preliminary activity.

It is yet a further object of the present invention to provide a system for controlling the communication of medical imaging data that enables the user to access various utilities available for use with the medical imaging data from a presently selected source without engaging in any preliminary activity.

It is still a further object of the present invention to provide a system for controlling the communication of medical imaging data that enables the user to access other functions of the system without engaging in any preliminary activity.

In order to overcome the deficiencies of the prior art and to achieve at least some of the objects and advantages listed, the invention comprises a system for controlling the communication of medical imaging data, including a computer, a plurality of sources of medical imaging data in communication with the computer, a plurality of destinations for the medical imaging data in communication with the computer, and a touchscreen controlled by the computer for simultaneously displaying a plurality of source icons and a plurality of destination icons, wherein the plurality of source icons correspond to the plurality of sources in order to allow a user of the system to select a particular source of medical imaging data, and the plurality of destination icons correspond to the plurality of destinations in order to allow the user to select at least one particular destination to receive the medical imaging data supplied by the selected source.

In some embodiments, the invention comprises a touchscreen that further includes a display window for displaying medical images generated from the medical imaging data supplied by the selected source.

In some of these embodiments, the display window is located between the plurality of source icons and the plurality of destination icons.

In some embodiments, the invention comprises a touchscreen that further includes a source indicator located adjacent the display window, wherein the source indicator corresponds to the selected source.

In some embodiments, the invention comprises a touchscreen that further includes a set of controls associated with the selected source.

In some of these embodiments, the set of controls is located below the display window.

In another embodiment, the invention comprises a system for controlling the communication of medical imaging data, including a computer, a plurality of sources of medical imaging data in communication with the computer, a plurality of destinations for the medical imaging data in communication with the computer, a touchscreen controlled by the computer, software executing on the computer for displaying on the touchscreen a plurality of source icons corresponding to the plurality of sources of medical imaging data in order to allow a user of the system to select a particular source of medical imaging data, and software executing on the computer for displaying on the touchscreen a plurality of destination icons corresponding to the plurality of destinations in order to allow the user to select at least one particular destination to receive the medical imaging data supplied by the selected source.

DETAILED DESCRIPTION OF THE DRAWINGS

Figure 1:
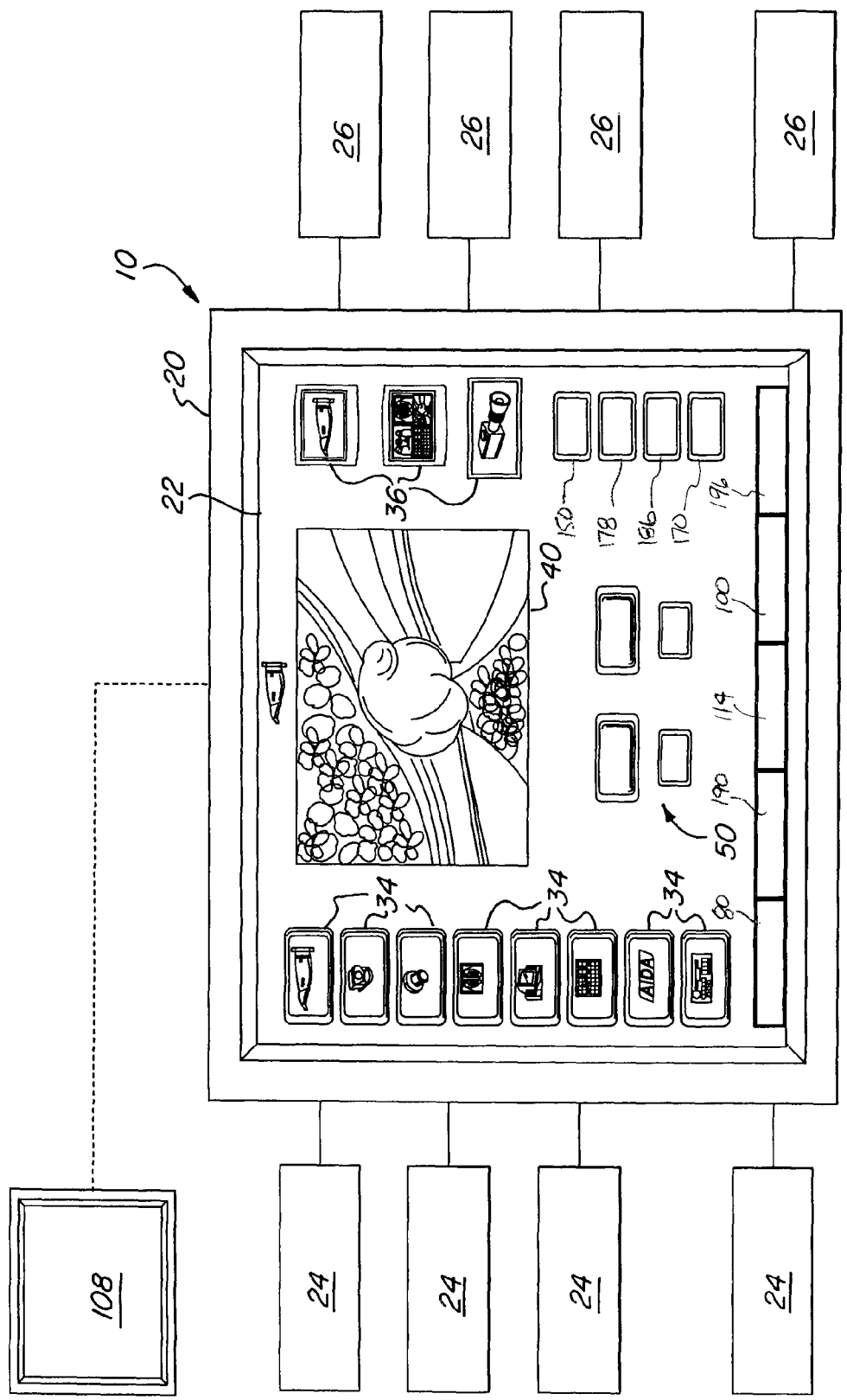
FIG. 1 is a schematic view of a system for controlling the communication of medical imaging data in accordance with the invention.

The basic components of one embodiment of a system for controlling the communication of medical imaging data in accordance with the invention are illustrated in FIG. 1. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

The system 10 includes a computer 20, a touchscreen 22 controlled by the computer 20, a plurality of sources 24 of medical imaging data connected to the computer 20, and a plurality of destinations 26 for the medical imaging data connected to the computer 20.

The sources 24 of medical imaging data connected to the computer 20 may include any devices, systems, or networks that generate, acquire, store, monitor, or control imaging data for use in generating medical images, such as still images or video. For example, the sources 24 may include image acquisition devices, such as endoscopic cameras, video endoscopes, room cameras, light cameras, and boom cameras. Likewise, the sources 24 may include any recording, storage, and/or archival devices or systems, such as traditional video cassette recorders or digital video recording devices (such as a linear tape deck or DVD recording device), image capture devices, a PACS (Picture Archiving and Communication System) computer, or a Hospital Information System. Finally, the sources 24 may include other devices from which medical imaging data may be received, such as a patient monitor or a central computer for controlling various devices, or may simply be auxiliary inputs for connecting external devices that may supply medical imaging data to the system.

Additionally, a source 24 may be a source of medical imaging data that receives medical imaging data from yet another source 24. For example, a source 24 may be a linear tape deck that is recording live video as it supplies the video to the computer 20. The linear tape deck, in turn, may receive the live video from an endoscopic camera presently being used on a patient, as is further described below. As another example, a source 24 may be a processor for routing images from multiple other sources 24 to the computer 20 (i.e., a screen splitter), such as a quad image processor, as is also further discussed below.

The destinations 26 for the medical imaging data supplied by the sources 24 may include any devices, systems, or networks that display medical images generated from the medical imaging data, or otherwise communicate the medical imaging data to viewers, or store the imaging data. For example, the destinations 26 may include any of various displays, such as, for example, a flat panel display, a plasma screen, or a computer monitor. Additionally, the destinations 26 may include a recording device or storage device, as described above.

Figure 2:
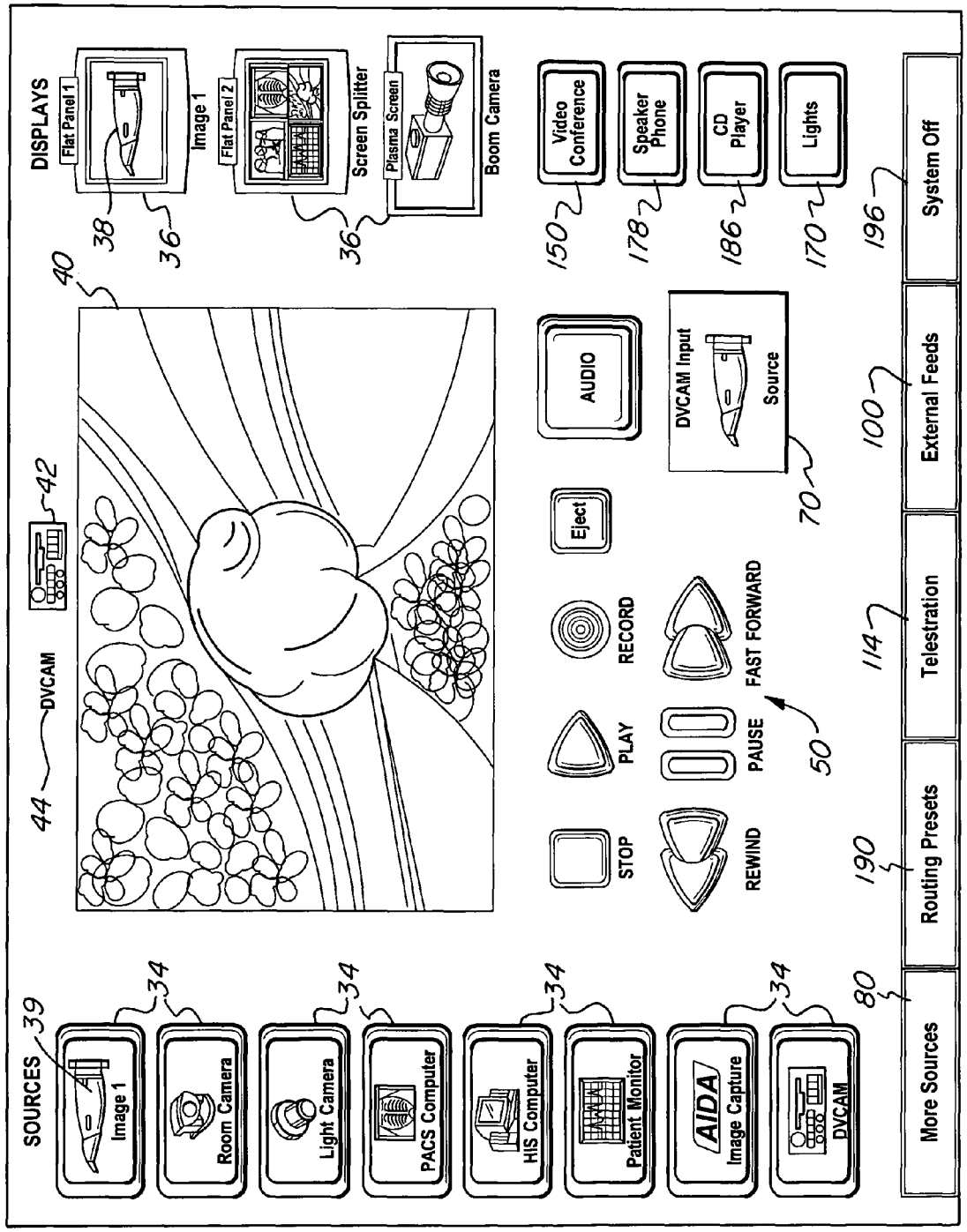
FIG. 2 is a screenshot of the touchscreen of the system of FIG. 1 when a linear tape deck is the selected source.
Figure 3:
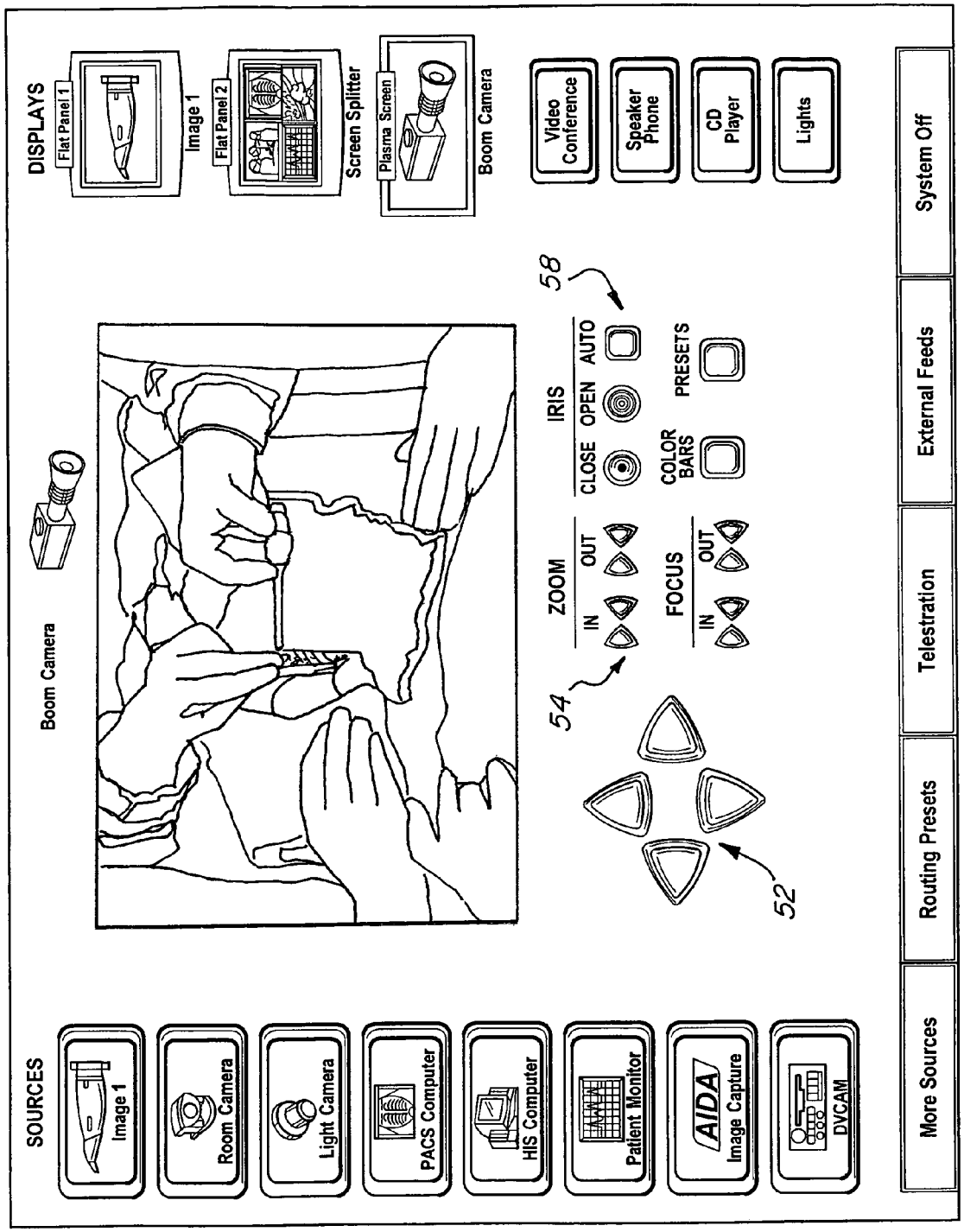
FIG. 3 is a screenshot of the touchscreen of the system of FIG. 1 when a boom camera is the selected source.
Figure 4:
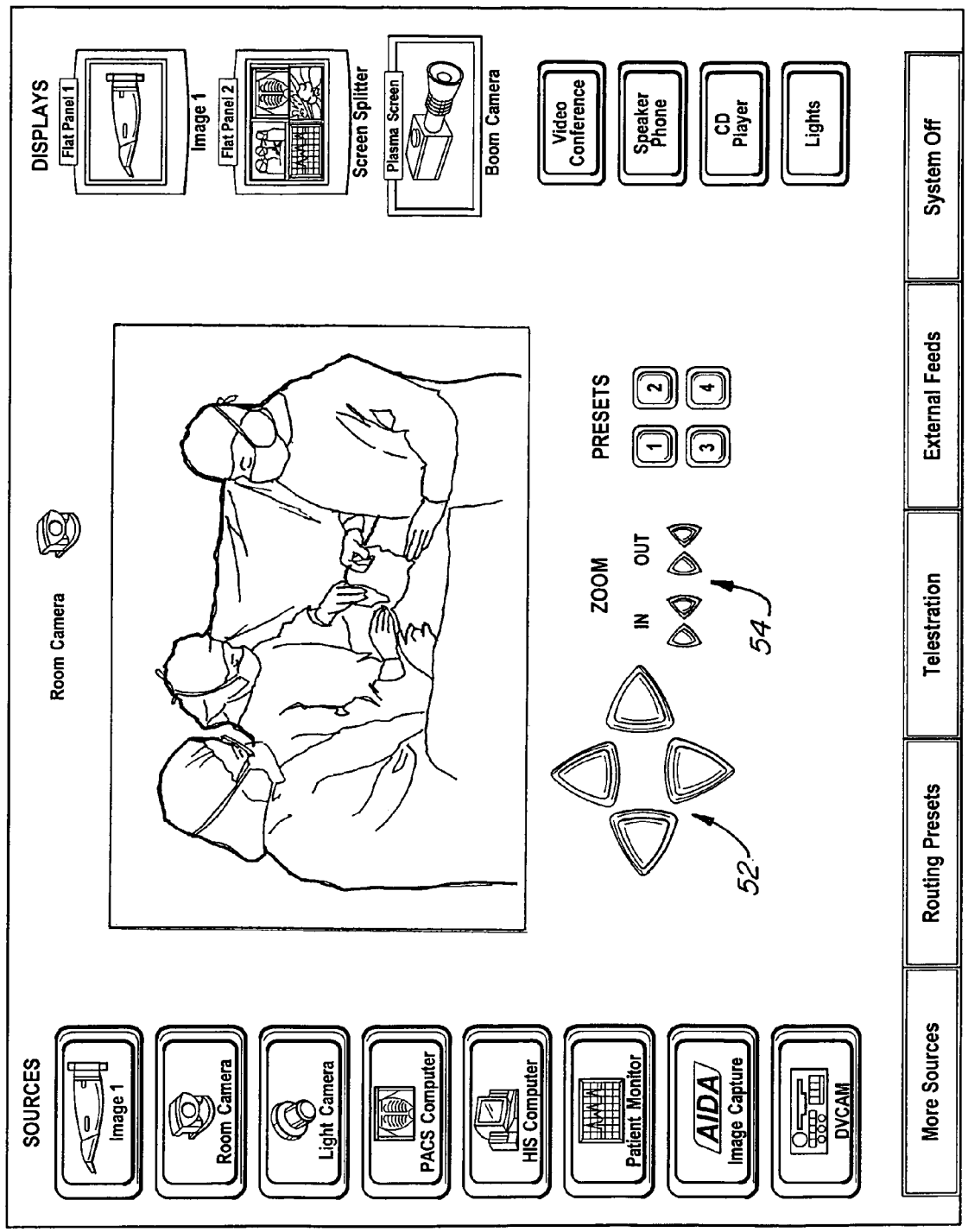
FIG. 4 is a screenshot of the touchscreen of the system of FIG. 1 when a room camera is the selected source.
Figure 5:
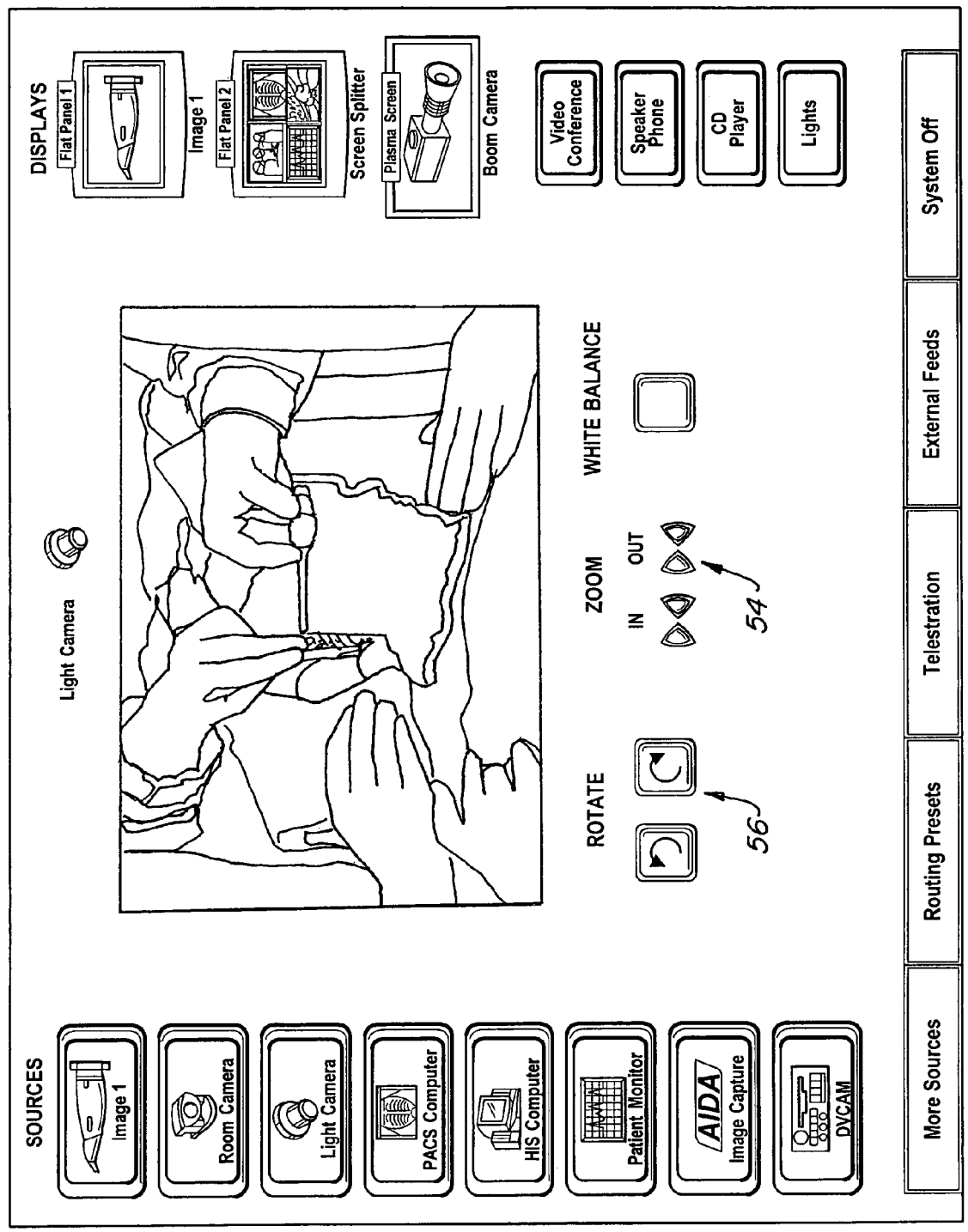
FIG. 5 is a screenshot of the touchscreen of the system of FIG. 1 when a light camera is the selected source.

As illustrated in FIGS. 1-2, the computer 20 includes software that cause the touchscreen 22 to simultaneously display a plurality of source icons 34 and a plurality of destination icons 36. The icons 34, 36 are sensitive to the touch of the user, such that the user can select particular sources and destinations 24, 26 by pressing the touchscreen 22 at the locations of the icons 34, 36, respectively. Accordingly, at any time, the user can simply choose a source 24 from among the plurality of sources represented by the source icons 34, and select the desired source by pressing the corresponding source icon 34. Similarly, the user can select a particular destination 26 for the medical imaging data being supplied by the selected source 24 by simply pressing the corresponding destination icon 36. If the user would like to choose an available source not presently displayed on the touchscreen, or the user would like to choose a destination that is remote (i.e., not in the surgical suite), the user may easily display palettes containing these additional sources and destinations, as is described further below.

In certain advantageous embodiments, at least some of the icons 34, 36 are virtual buttons, such that user gets the impression he or she is pressing a three dimensional object. In some embodiments, certain icons 34 include a graphic representing the corresponding source 24, such as a graphical representation of the corresponding source 24 or a logo representing the corresponding source 24. In some embodiments, certain icons 34 may include both a graphical representation of the source 24 and a logo representative thereof, while certain icons 34 may simply identify the corresponding source 24 with text or a symbol. In certain advantageous embodiments, the destination icons 36 include a source indicator 38 that corresponds to the particular source 24 selected for that particular destination 26. In these embodiments, the source indicator 38 is the same graphic, text, and/or other indicia 39 that is present on the source icon 34 for the selected source 24.

The touchscreen 22 also includes a display window 40, which displays medical images generated from the medical imaging data supplied by the presently selected source 24. In this way, the user can preview the images being routed to at least one of the destinations 26. When used with a screen splitter, as further described below, the user can preview images from multiple sources 24 at once. In certain advantageous embodiments, the user can also manipulate or alter the images being displayed in the window 40 in order to affect the images ultimately being communicated to the destinations 26. In some embodiments, the display window 40 is located between the source icons 34 and the destination icons 36.

In certain advantageous embodiments, a source indicator 42 is displayed adjacent the window 40. The source indicator 42 identifies the source 24 of the medical imaging data that is being used to generate the images presently displayed in the window 40. The indicator 42 may include a graphic, such as a graphical representation of, or a logo corresponding to, the presently selected source 24. In certain embodiments, text 44 identifying the source 24 is also displayed next to the source indicator 42. In some embodiments, the source indicator 42 and/or text 44 is located above the window 42.

The touchscreen 22 also includes a set of controls 50 associated with the selected source 24, allowing the user to actively control the selected source 24 based on the images the user is viewing in the display window 40. In certain advantageous embodiments, the controls are virtual buttons, thereby providing the user with the illusion that he or she is pressing a three dimensional control. In some embodiments, the set of controls 50 is located below the window 40.

Figure 6:
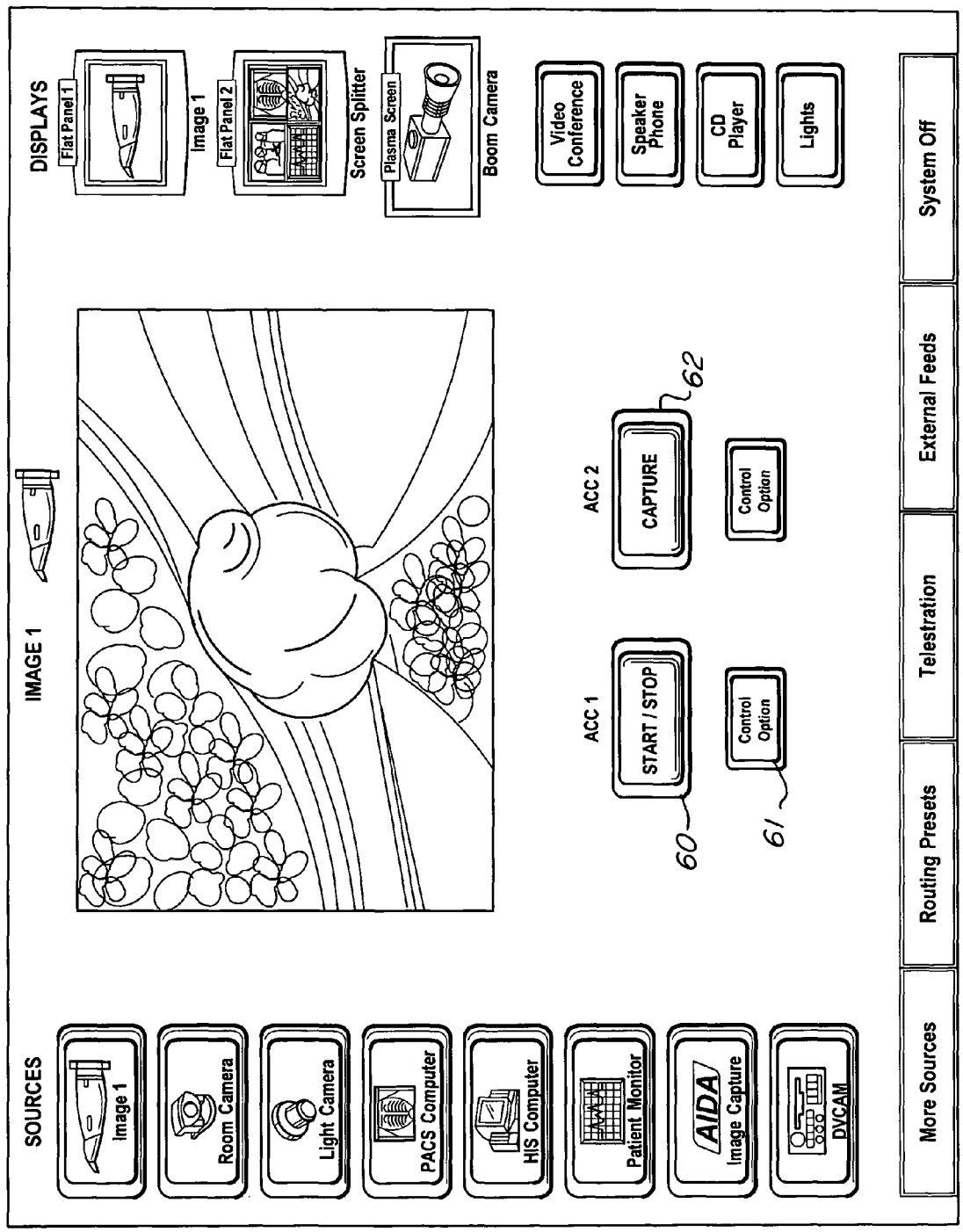
FIG. 6 is a screenshot of the touchscreen of the system of FIG. 1 when an endoscopic camera is the selected source.
Figure 7:
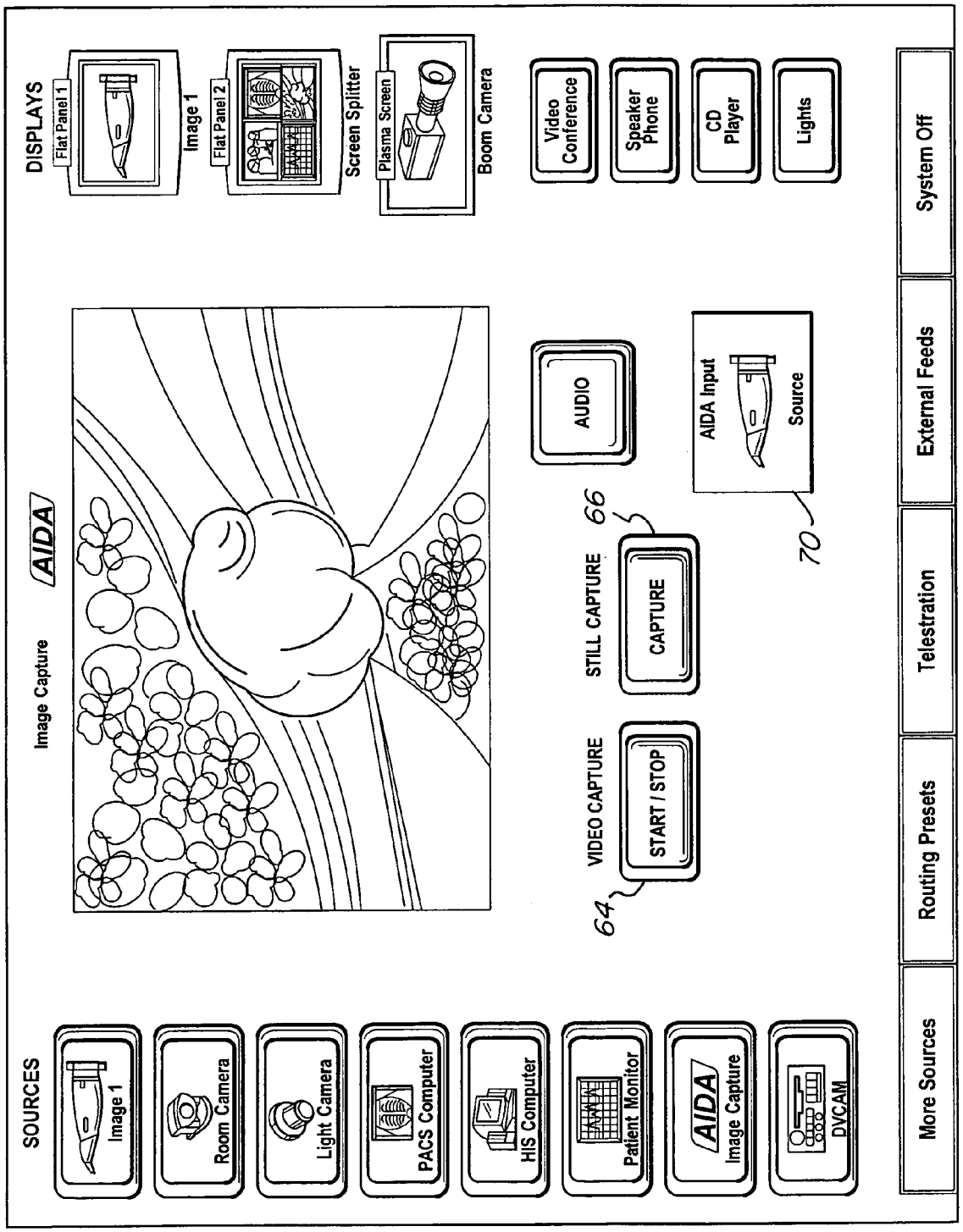
FIG. 7 is a screenshot of the touchscreen of the system of FIG. 1 when an image capture device is the selected source.

As illustrated in FIGS. 2-7, the set of controls 50 includes controls that are specific to the source 24 that has been selected by the user. Therefore, as shown in FIG. 2, if the presently selected source 24 is a tape deck, the controls may include play, stop, rewind, fast forward, and record buttons. On the other hand, referring to FIGS. 3-5, if the presently selected source 24 is a boom camera, a room camera, or a light camera, the controls may include panning buttons 52 for changing the field of view of the camera, zoom buttons 54 for zooming in and out, rotation buttons 56 for rotating the camera, or iris buttons 58 for controlling the opening and closing of an iris. Referring to FIG. 6, if the presently selected source 24 is an endoscopic camera, the set of controls 50 may instead include a button 60 for starting and stopping the live video in order to temporarily view frozen images, as well as a capture button 62 for saving certain frozen images. Similarly, as shown in FIG. 7, if the presently selected source 24 is an image capture device (which is, in turn, receiving imaging data from an endoscopic camera), the set of controls may include a button 64 for starting and stopping the recording of video, as well as a button 66 for storing individual still images.

Figure 8:
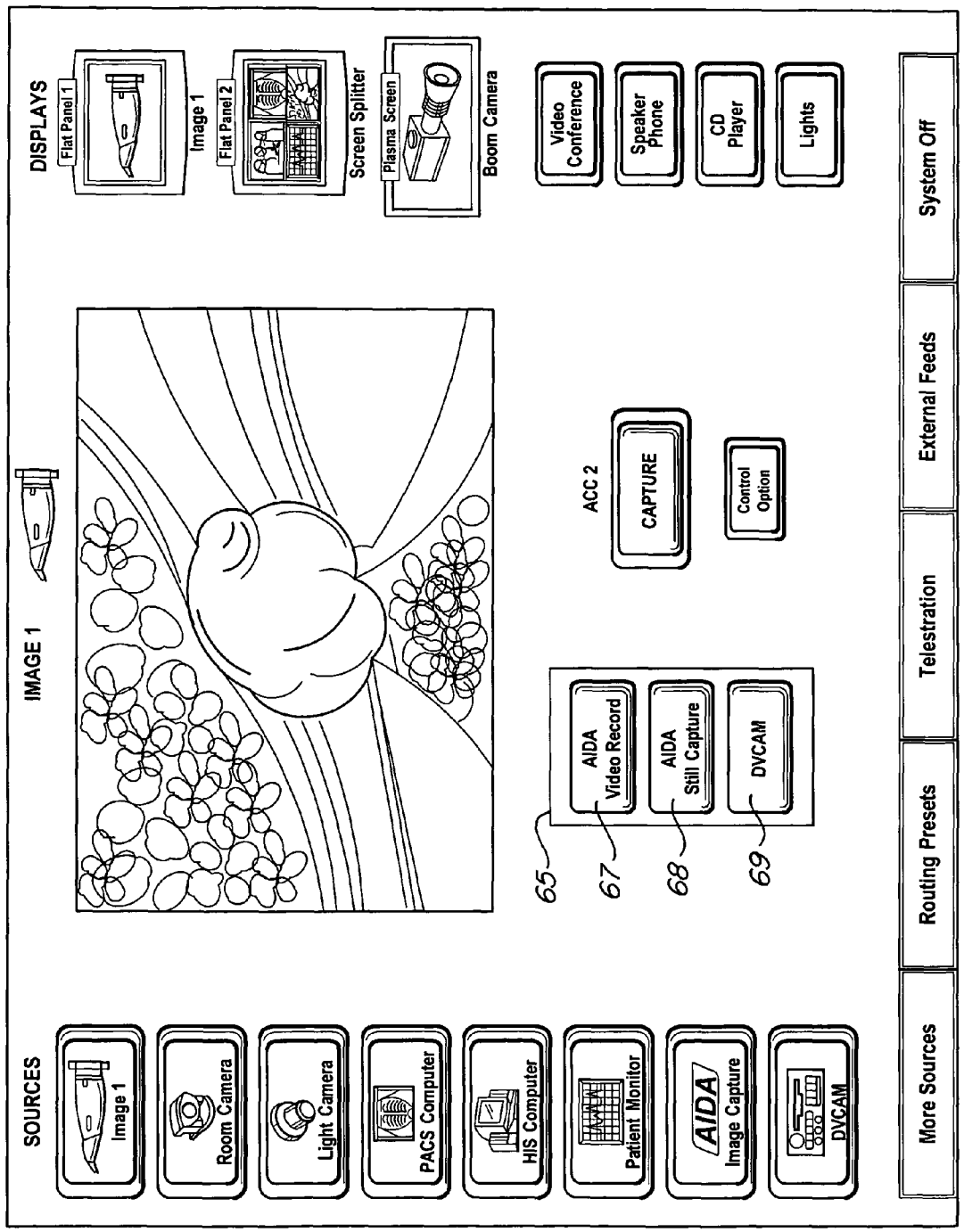
FIG. 8 is a screenshot of the touchscreen of the system of FIG. 1 when a control options icon has been pressed.

In certain advantageous embodiments, the controls 50 may also include a control for customizing the controls 50 themselves. For example, as illustrated in FIGS. 6 and 8, the user may press a control option button 61, which displays a control selection palette 65. From the palette 65, the user can select a particular function for button 60. For example, FIG. 6 shows button 60 as a "start/stop" button for starting and stopping the recording of video by an AIDA recording device. By pressing the control option button 61, and then, on the palette 65 that is displayed, pressing the AIDA still capture button 68, the button 60 will change into a "capture" button (presently shown under ACC 2), thereby allowing the user to use button 60 to capture still images to the AIDA device. In this way, the user can simulate real buttons on the source 24 itself that can be utilized for different functions, such as programmable buttons on an endoscopic camera head.

Additionally, as illustrated in FIGS. 2 and 7, if the presently selected source 24 is a recording device, the set of controls 50 includes a source selection icon 70 for selecting a source from which the presently selected source 24 receives medical imaging data prior to communicating that data to the computer 20, as is further described below.

The operation of the system 10 will now be described primarily with reference to FIGS. 1-2, as well as other individual figures as specifically identified. The user typically begins by touching the touchscreen 22, which may or may not initially display an introductory screen displaying the manufacturer's logo or the like (not shown), which then displays to the user a screen similar to that illustrated in FIG. 2, including source icons 34, destination icons 36, display window 40, and a set of controls 50.

Figure 9:
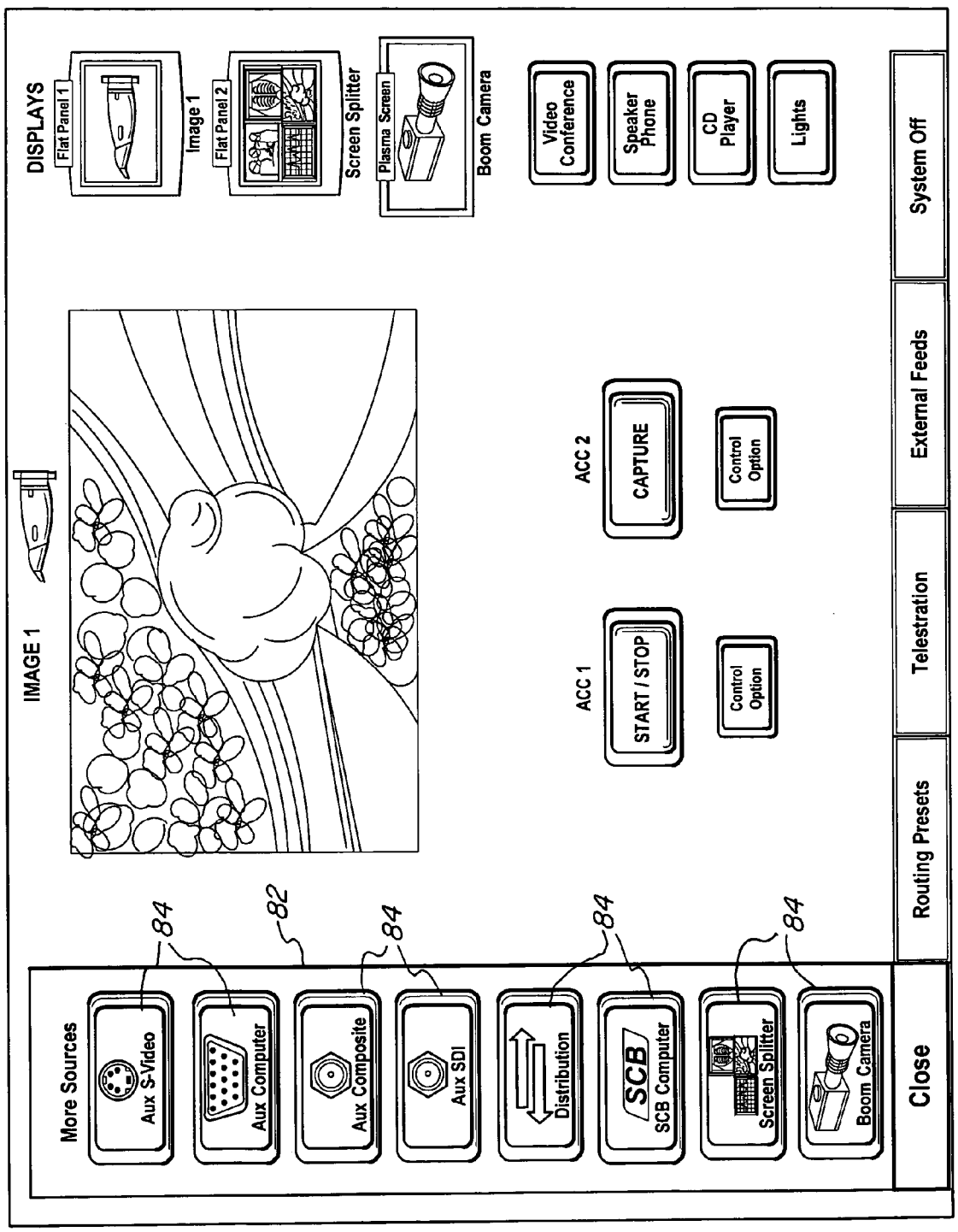
FIG. 9 is a screenshot of the touchscreen of the system of FIG. 1 when an additional sources icon has been pressed.

The user chooses a particular source 24 of medical imaging data that he or she would like to route to at least one destination 26, and reviews the plurality of source icons 34 displayed on the touchscreen 22. If the user does not see an icon 34 corresponding to the particular source 24 that he wants to route, the user can press an additional sources icon 80 located at the bottom of the touchscreen 22. As illustrated in FIG. 9, pressing icon 80 displays a palette 82 of additional source icons 84. The icons 84 correspond to additional sources, and the user may select one of these additional sources by simply pressing the corresponding icon 84. In some embodiments, the palette 82 is superimposed over the sources icons 34 and, after a predetermined period of time (e.g., five seconds), will disappear.

When the user presses a source icon 34 (or additional source icon 84), thereby selecting a particular source, the images appearing in the display window 40 will change to images generated from the imaging data supplied from the newly selected source, the set of controls 50 will change to controls associated with the newly selected source, and the source indicator 42 and/or identifying text 44 will change to reflect the newly selected source 24.

Figure 10:
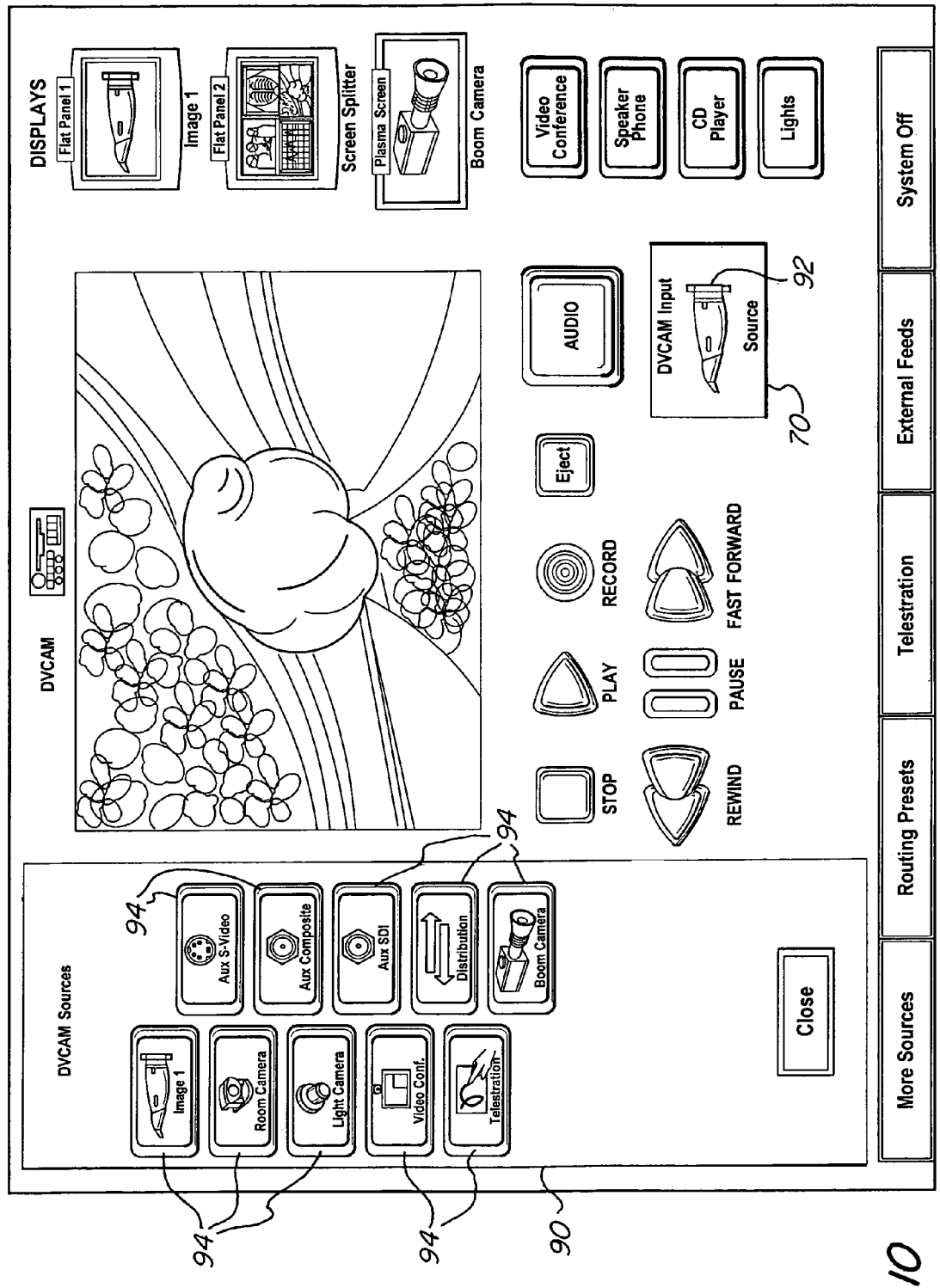
FIG. 10 is a screenshot of the touchscreen of the system of FIG. 1 when a source selection icon has been pressed.

If the newly selected source 24 is a recording device, the user may choose another source, from which the newly selected source 24 receives medical imaging data, by pressing the source selection icon 70. As shown in FIG. 10, when the user presses icon 70, the touchscreen 22 displays a palette 90 of icons 94. The icons 94 correspond to available sources from which the presently selected source 24 can receive medical imaging data prior to communicating that data to computer 20. When an icon 94 is pressed, and the corresponding source of medical imaging data for the presently selected source 24 is thereby selected, a source indicator 92, which represents the other source from which the presently selected source 24 is receiving medical imaging data, appears in the source selection icon 70. Accordingly, the user always knows which other source is supplying the imaging data to the presently selected source 24.

Once a source 24 of medical imaging data (and possibly, a source for that source) has been selected, the user may then select a particular destination 26 from among the plurality of available destinations 26 to receive the medical imaging data from the presently selected source 24 by pressing any of the destination icons 36. In this way, the user may select one, some, or all of the destinations 26 to receive the medical imaging data being supplied from the presently selected source 24. As each destination icon 36 is pressed, the medical imaging data being supplied by the presently selected source 24 and producing the images presently being viewed in the display window 40 is communicated to the corresponding destination 26, and a source indicator 38, which represents the presently selected source 24 from which that destination is receiving medical imaging data, appears in the destination icon 36. Accordingly, the user always knows which source is supplying the data for the medical images presently being viewed at any particular destination 26.

Figure 11:
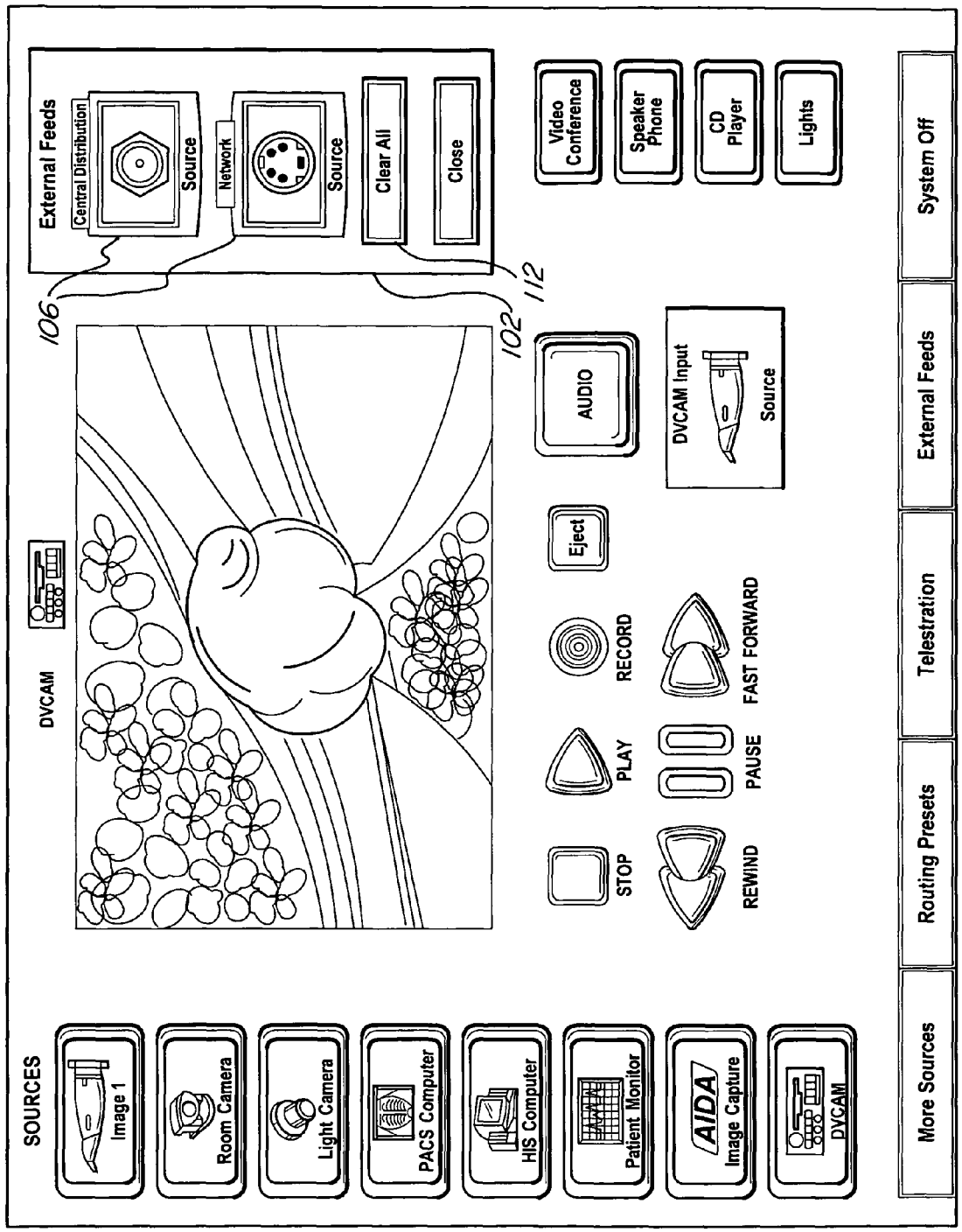
FIG. 11 is a screenshot of the touchscreen of the system of FIG. 1 when an external feeds icon has been pressed.

If the user desires to send the medical imaging data to a remote destination 108, the user can press an external feeds icon 100 located at the bottom of the touchscreen 22. As shown in FIG. 11, pressing icon 100 displays a palette 102 of remote destination icons 106. The icons 106 correspond to remote destinations 108 (FIG. 1) to which the medical imaging data can be communicated, and the user may select one of these remote destinations 108 by simply pressing the corresponding icon 106. In some embodiments, the palette 102 is superimposed over the destination icons 36 and, after a predetermined period of time (e.g., five seconds), will disappear.

Figure 12:
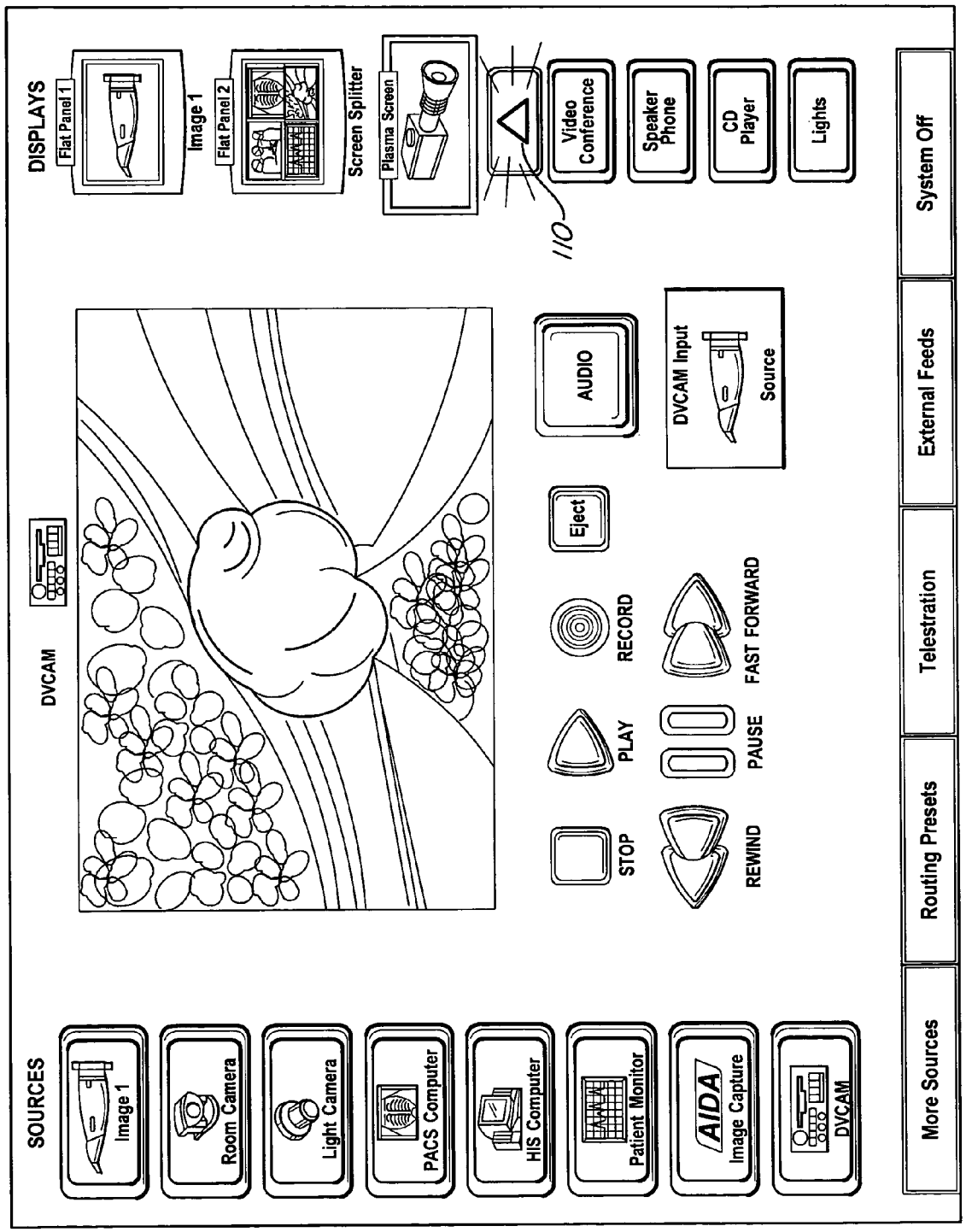
FIG. 12 is a screenshot of the touchscreen of the system of FIG. 1 when an remote destination has been selected.

As illustrated in FIG. 12, in certain advantageous embodiments, a caution indicator 110 will appear to remind the user that medical imaging data is being communicated to remote destinations 108, which has important implications with respect to patient privacy. The indicator 110 may, for example, be a red blinking caution symbol, and in some embodiments, is also an active button that, when pressed, again displays the palette 102. Additionally, the palette 102 includes a termination icon 112, enabling the user to terminate the communication of medical imaging data to all remote destinations 108 with a single press.

Figure 13:
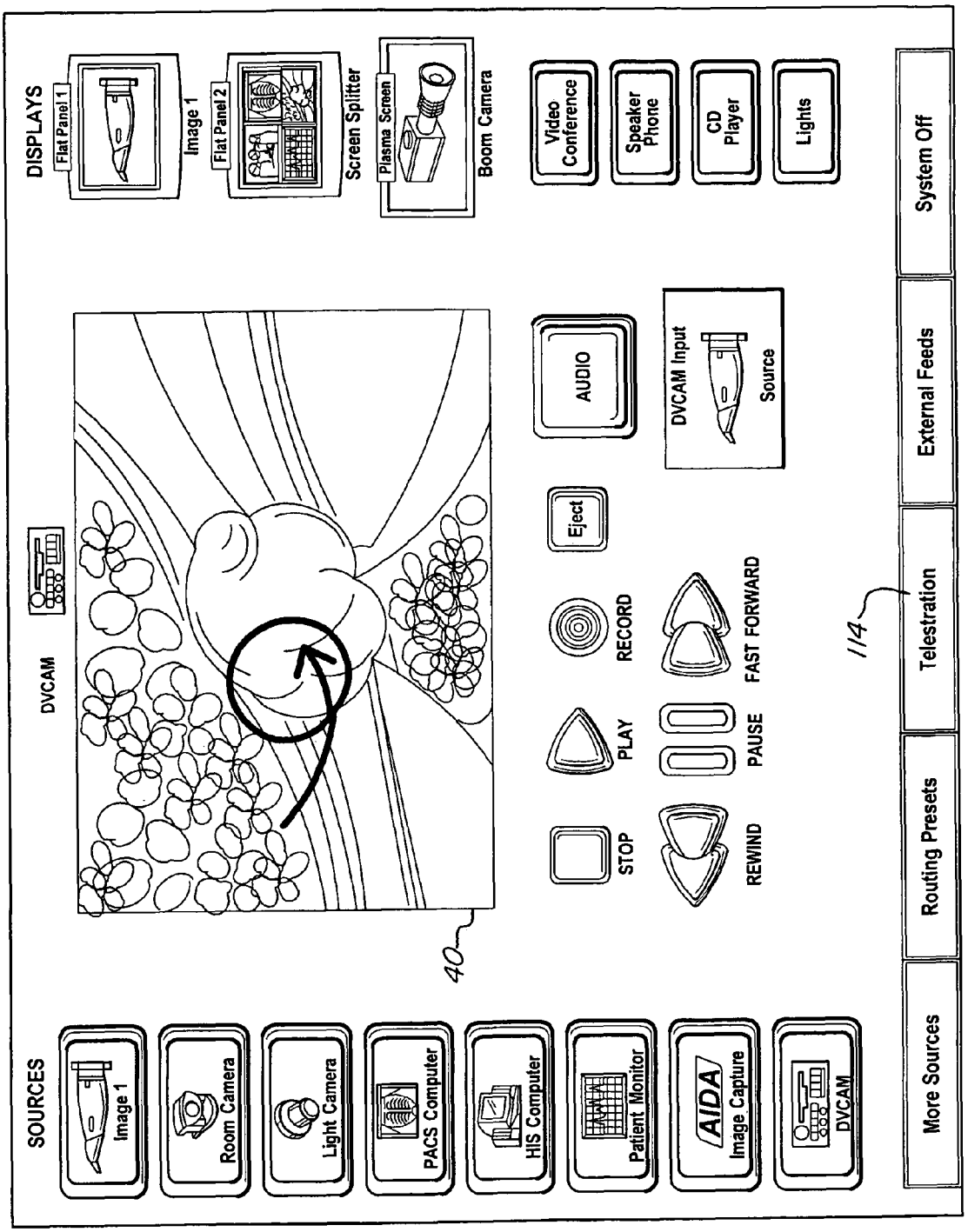
FIG. 13 is a screenshot of the touchscreen of the system of FIG. 1 during telestration.

If the user wants to make marks on the images, such as circling particular areas of interest, or otherwise annotate the images, the user can press a telestration icon 114 located at the bottom of the touchscreen 22. As shown in FIG. 13, the user will then be able to mark the images being routed from the presently selected source 24 by drawing on the images appearing in the display window 40 with the user's finger.

Alternatively, the user may enter the telestration utility by selecting it as a source. As previously explained with reference to FIG. 10, when the presently selected source 24 is a recording device, an additional source may be selected to supply medical imaging data to that source. In the example shown in FIG. 10, a linear tape deck (DVCAM) has been selected as the source 24, and an endoscopic camera (Image 1) has, in turn, been selected as the source for the linear tape deck. Accordingly, video flows from the endoscopic camera, through the tape deck (where it can be recorded), and is displayed in the window 40. The user can press the source selection icon 70 to display the palette 90, and can then press a telestration button thereon. As a result, the user will be able to telestrate over the images coming from the endoscopic camera, through the tape deck, and displayed in the window 40. Accessing the telestration utility in this manner allows the user to record the telestration on the tape deck, in contrast to the use of the button 114, which simply displays the telestration in the window 40 and sends it to the selected destinations 26, but does not record it on the tape deck.

Figure 14:
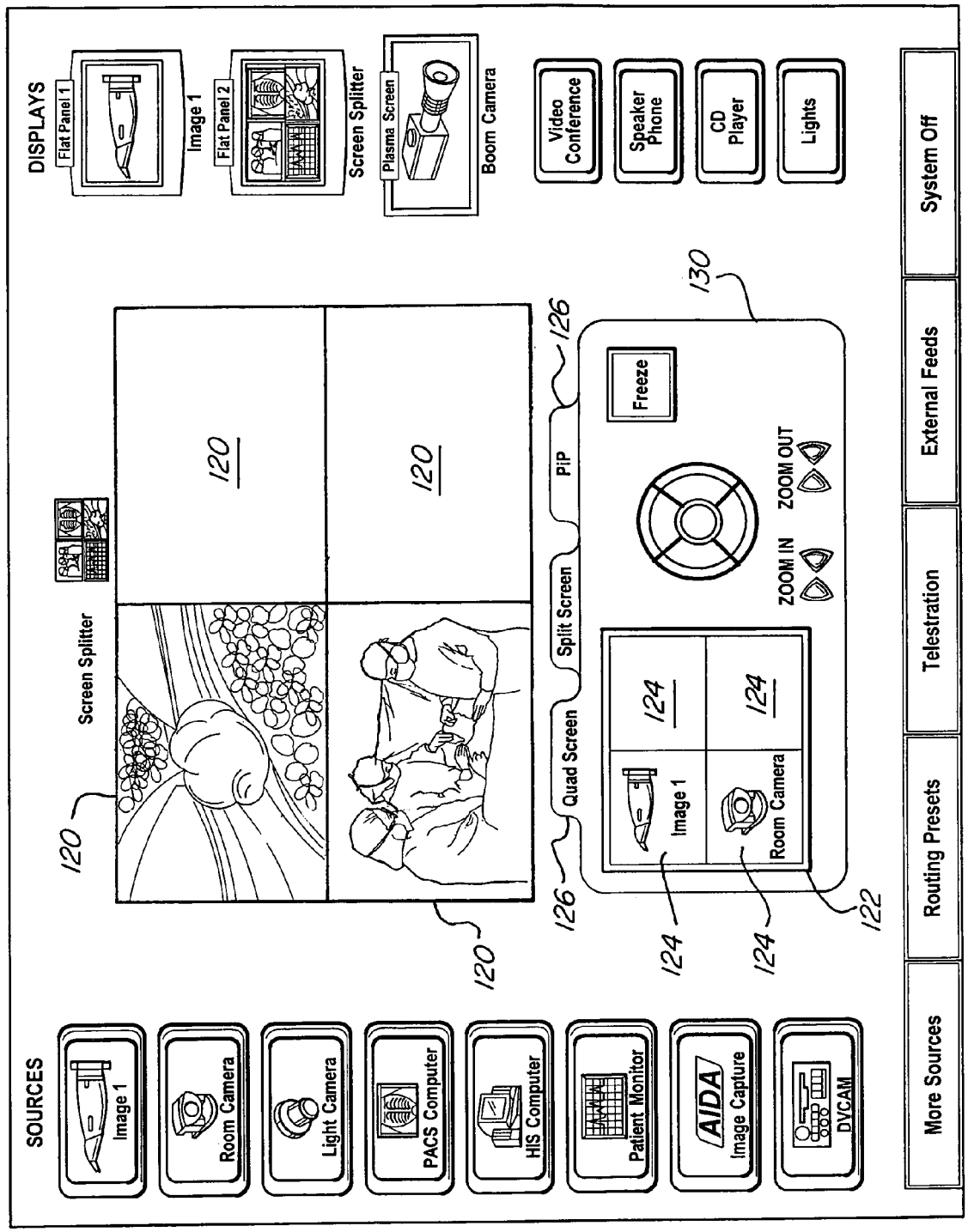
FIG. 14 is a screenshot of the touchscreen of the system of FIG. 1 when a screen splitter is the selected source and the screen splitter is in quad image mode.

If the user desires to view medical images generated from multiple sources 24 simultaneously, the user can select a screen splitter, such as a quad image processor, as the source of medical imaging data by pressing the corresponding icon 34. As illustrated in FIG. 14, upon selecting the screen splitter as the source (i.e., pressing the screen splitter icon 84 in FIG. 9), the display window 40 divides into a plurality of sections 120 for separately displaying medical images generated from medical imaging data supplied by a plurality of other sources 24. At the same time, the set of controls 50 changes to controls associated with the screen splitter. These controls include a source selection panel 122 having a plurality of sections 124 corresponding to the plurality of sections 120 in the display window 40. Accordingly, in order to make medical images generated from a particular source 24 appear in a particular section 120, the user presses the corresponding section 124 in panel 122, and then presses the source of medical images desired for that particular section 120.

Figure 15:
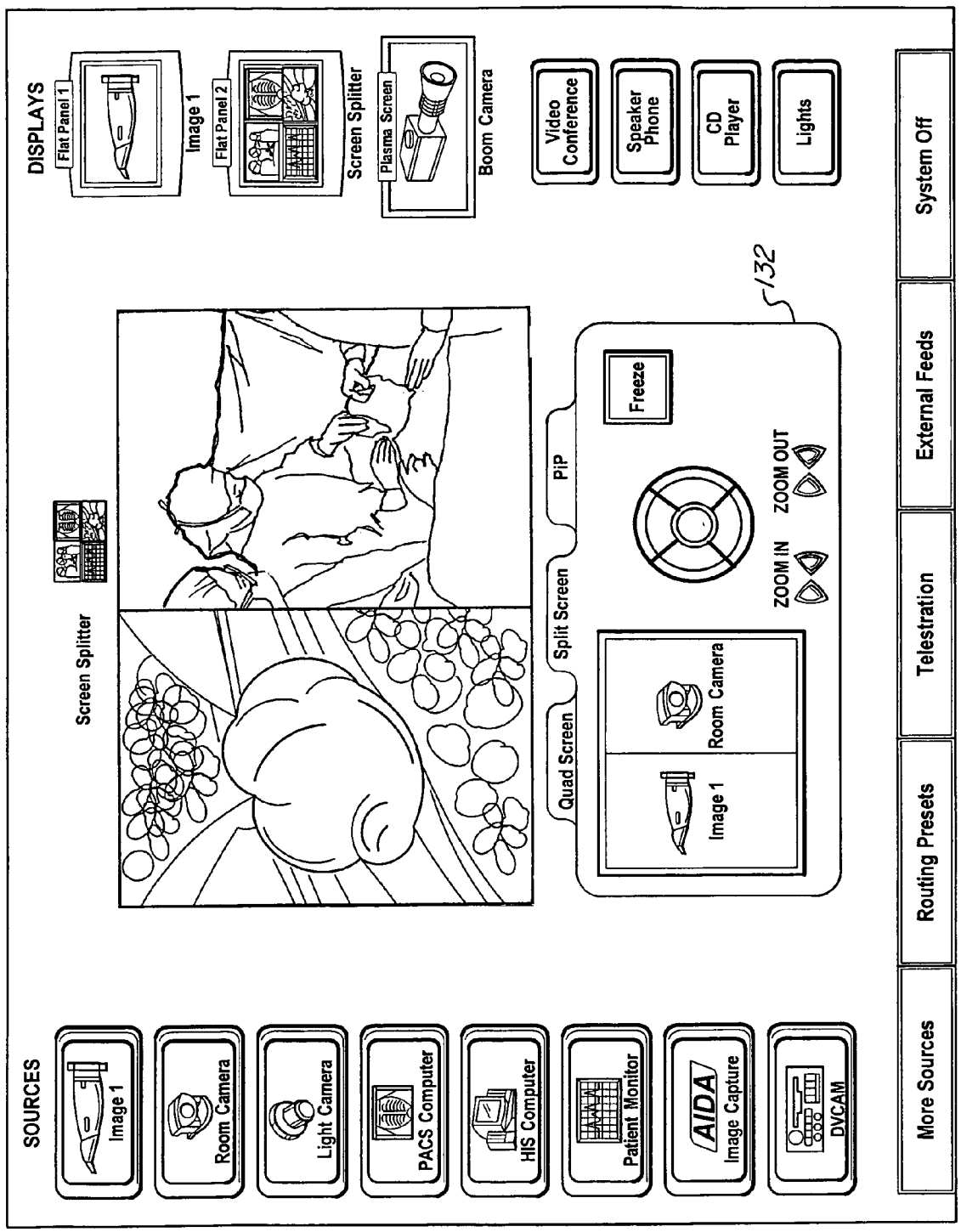
FIG. 15 is a screenshot of the touchscreen of the system of FIG. 1 when a screen splitter is the selected source and the screen splitter is in dual image mode.
Figure 16:
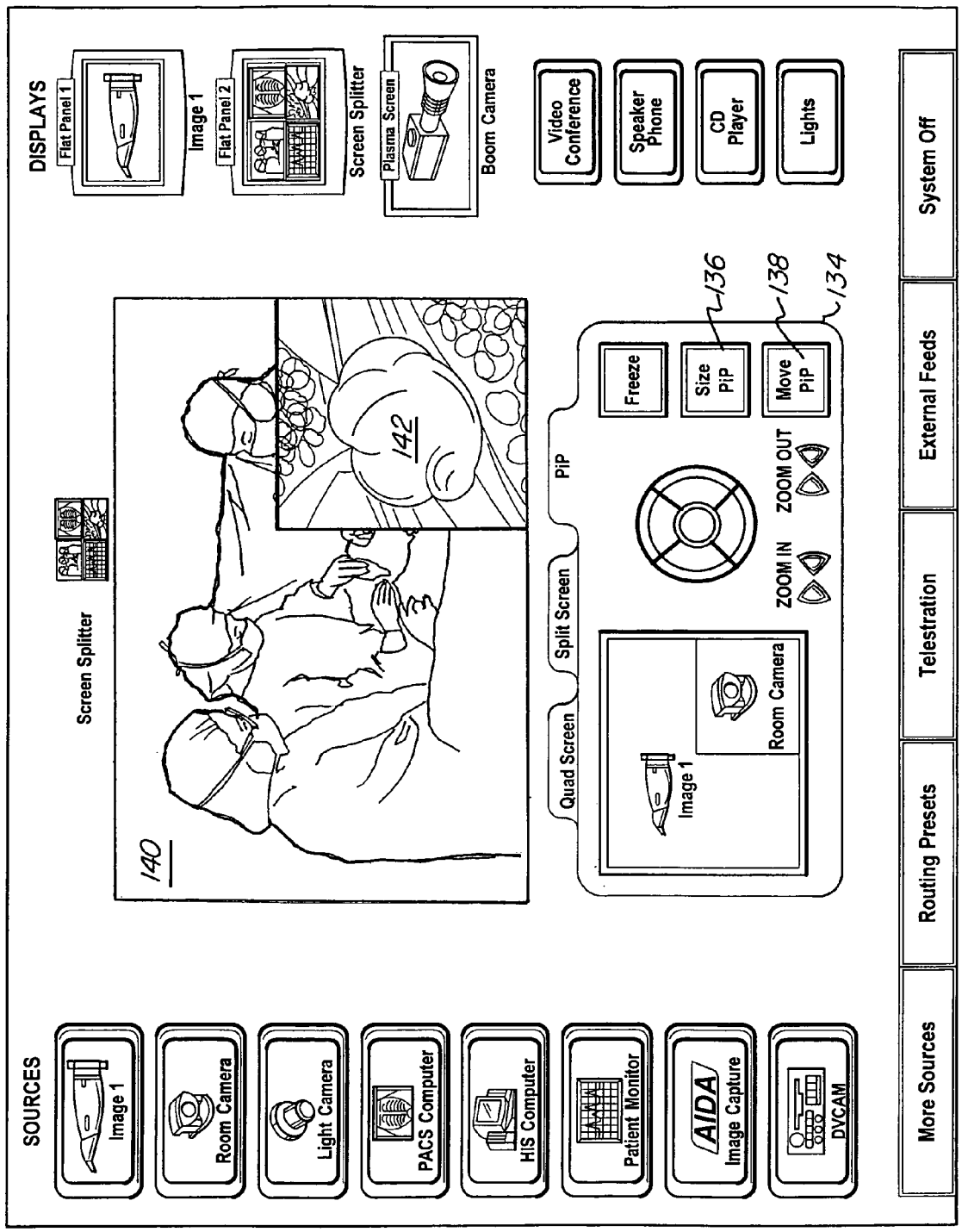
FIG. 16 is a screenshot of the touchscreen of the system of FIG. 1 when a screen splitter is the selected source and the screen splitter is in picture-in-picture mode.

As illustrated in FIGS. 14-16, in certain advantageous embodiments, the set of controls 50 includes mode selectors 126, which allow the user to select one of a plurality of alternate modes, and thereby switch between different control panels 130, 132, 134 corresponding to the different modes. For example, the different modes may include quad image (FIG. 14), dual image (FIG. 15), or picture-in-picture (FIG. 16). When in picture-in-picture mode, the display window 40 includes a large section 140 for displaying a large image, and a smaller section 142 within the larger section 140 for displaying a smaller image. In some of these embodiments, the control panel 134 includes a size icon 136 for changing the size of the smaller section 142, and in some embodiments, the panel 134 includes a position icon 138 for changing the location of the smaller section 142 within the larger section 140.

Figure 17:
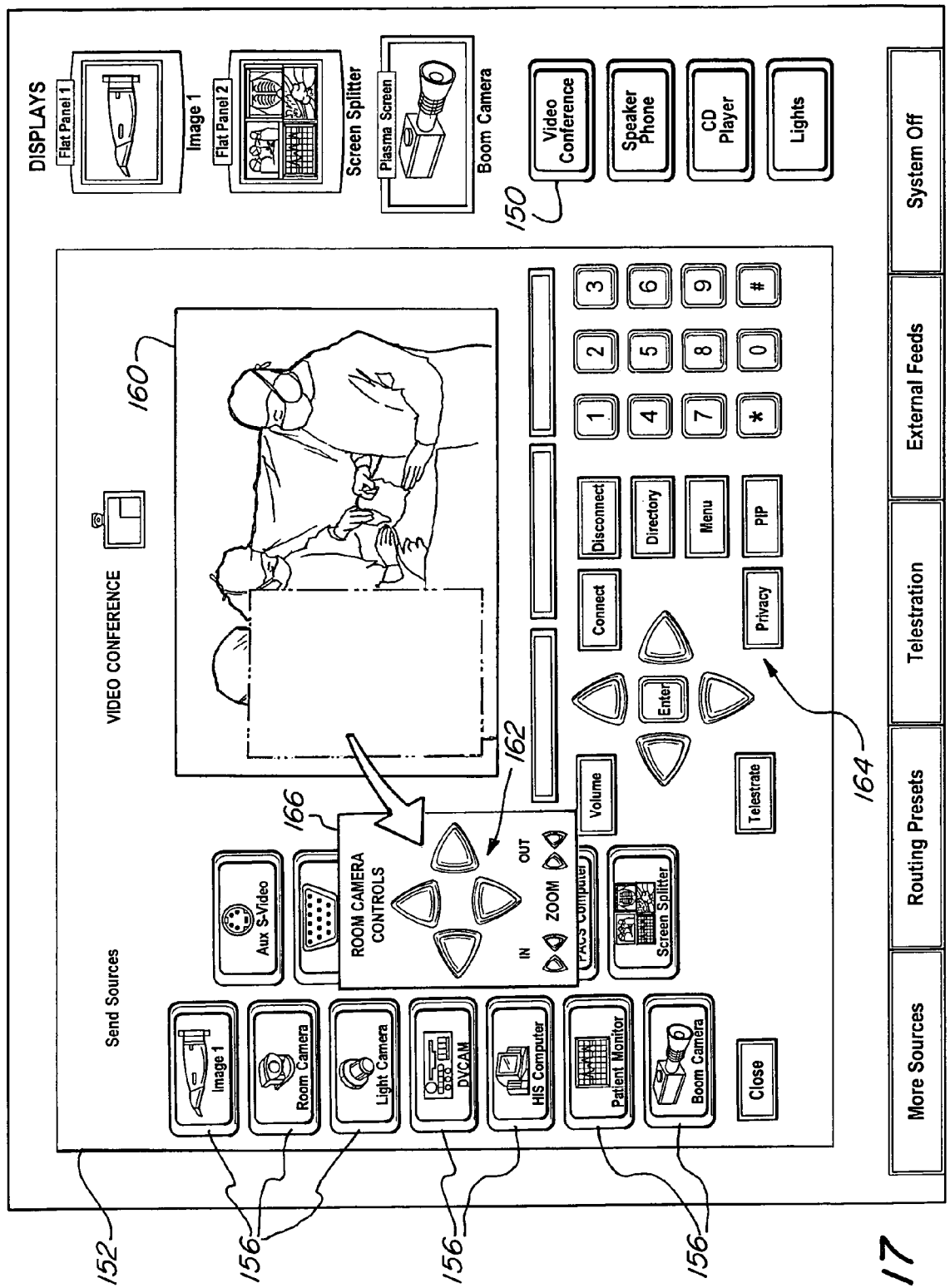
FIG. 17 is a screenshot of the touchscreen of the system of FIG. 1 during a videoconference.

If the user wants to communicate images to a remote individual during a videoconference, the user can press a videoconference icon 150. As illustrated in FIG. 17, when icon 150 is pressed, a videoconferencing interface 152 is displayed on the touchscreen 22. The interface 152 includes source icons 156, which correspond to the selectable sources from which medical imaging data can be communicated to the remote user. The interface 152 also includes a display window 160 for displaying medical images generated from the imaging data supplied by the selected source. Additionally, the interface 152 includes a set of controls 162 associated with the selected source, as well as a set of controls 164 associated with video conferencing. In certain embodiments, the set of controls 162 are part of a control panel 166 that is movable around the interface 152.

In certain advantageous embodiments, when the selected source is a recording device, video conferencing may alternatively be selected as a source, as similarly described previously for telestration. Referring to FIG. 10, the plurality of source icons 94 includes a video conferencing icon. As with telestration, by pressing the source selection icon 70 to display the palette 90, and then pressing the video conference button on palette 90, the video conference itself can be recorded by the presently selected source 24 (e.g., linear tape deck).

Figure 18:
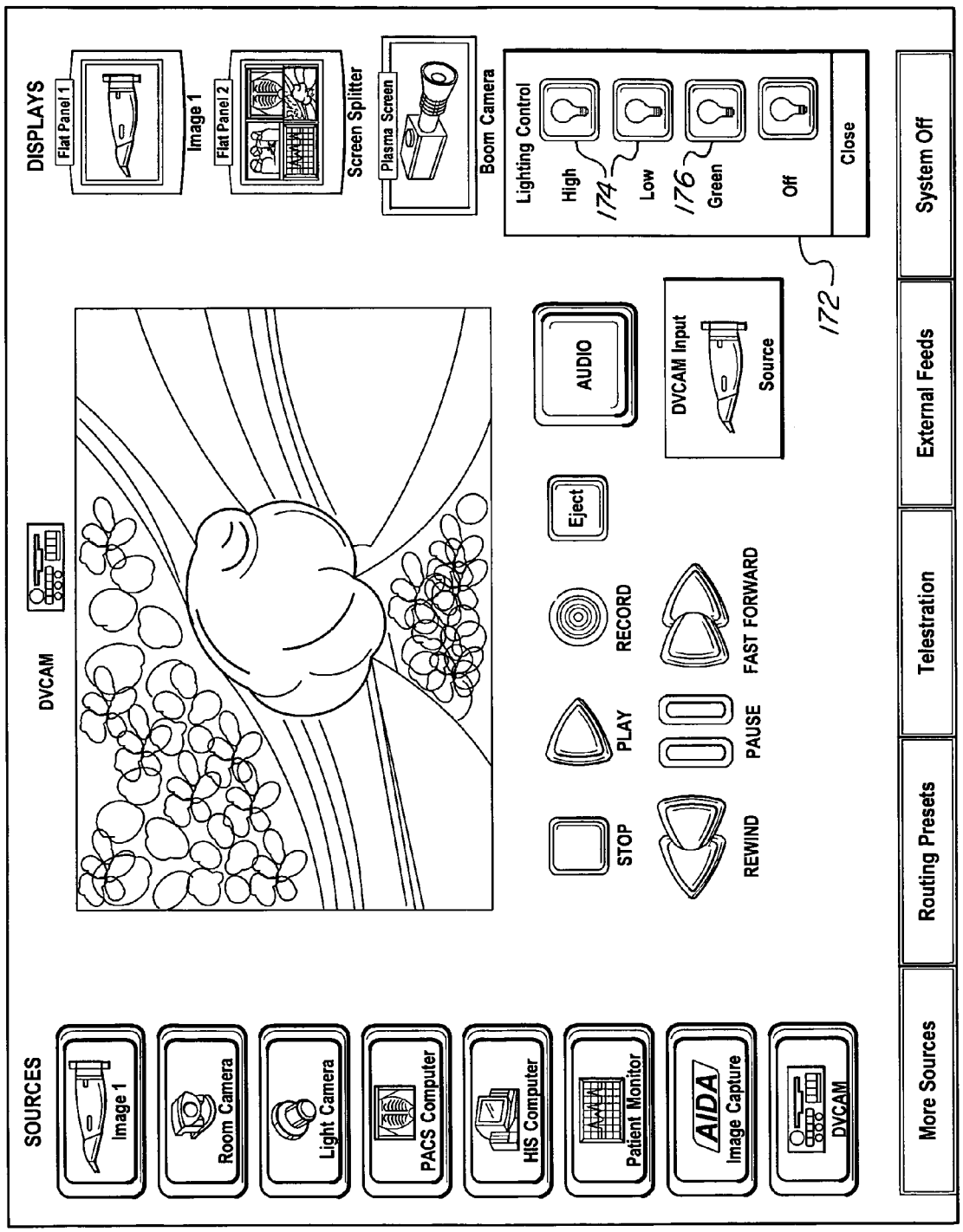
FIG. 18 is a screenshot of the touchscreen of the system of FIG. 1 when a lighting icon has been pressed.

In addition to selecting and controlling various sources and destinations of medical imaging data, and routing, altering, recording, and viewing that data, the user can also control several other items from the touchscreen 22. For example, the user can press a lighting icon 170 (FIG. 2) to display a palette 172 of lighting controls, as illustrated in FIG. 18. The palette 172 may, for example, include buttons 174 for adjusting light intensity or buttons 176 for adjusting color.

Figure 19:
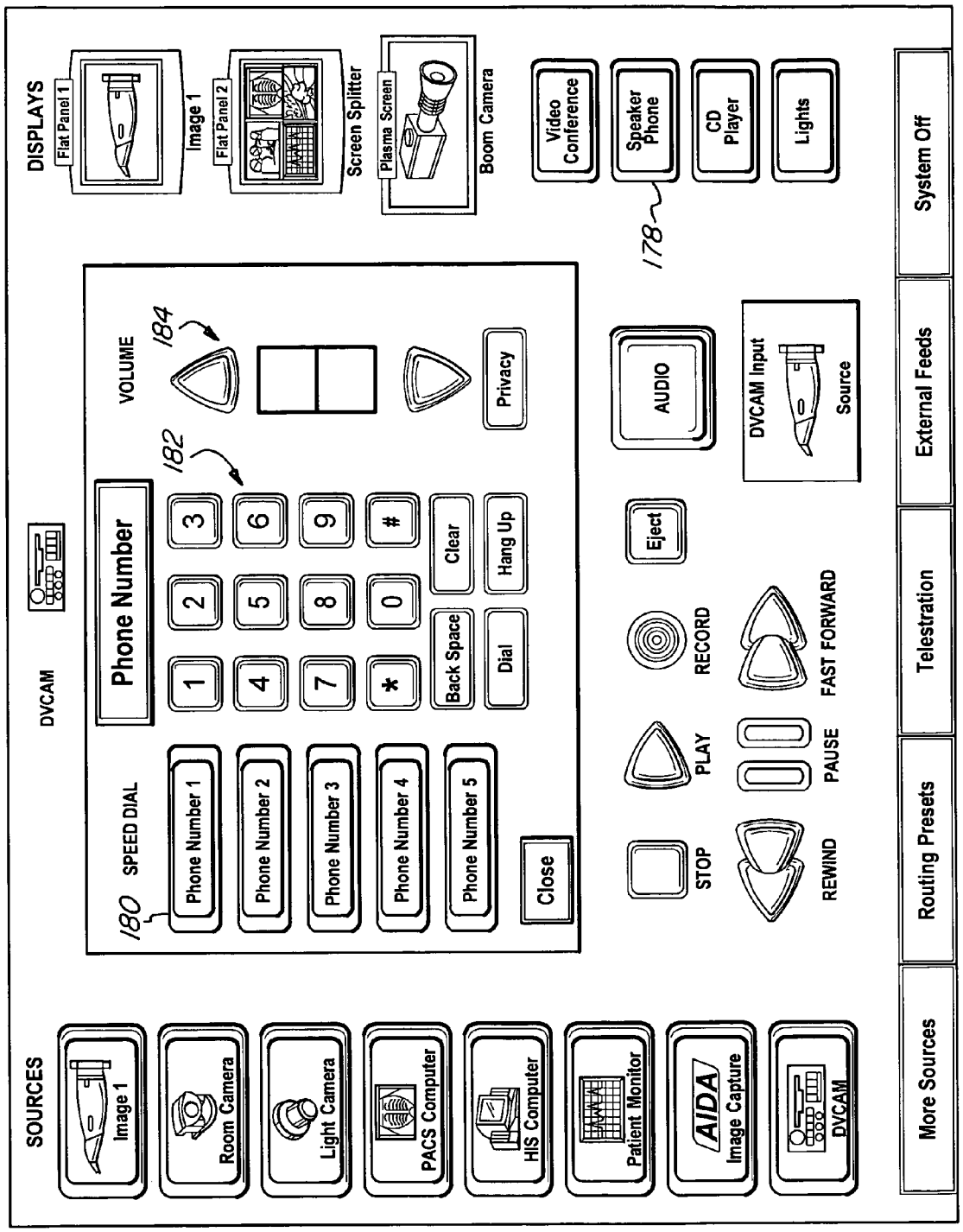
FIG. 19 is a screenshot of the touchscreen of the system of FIG. 1 when a speakerphone icon has been pressed.
Figure 20:
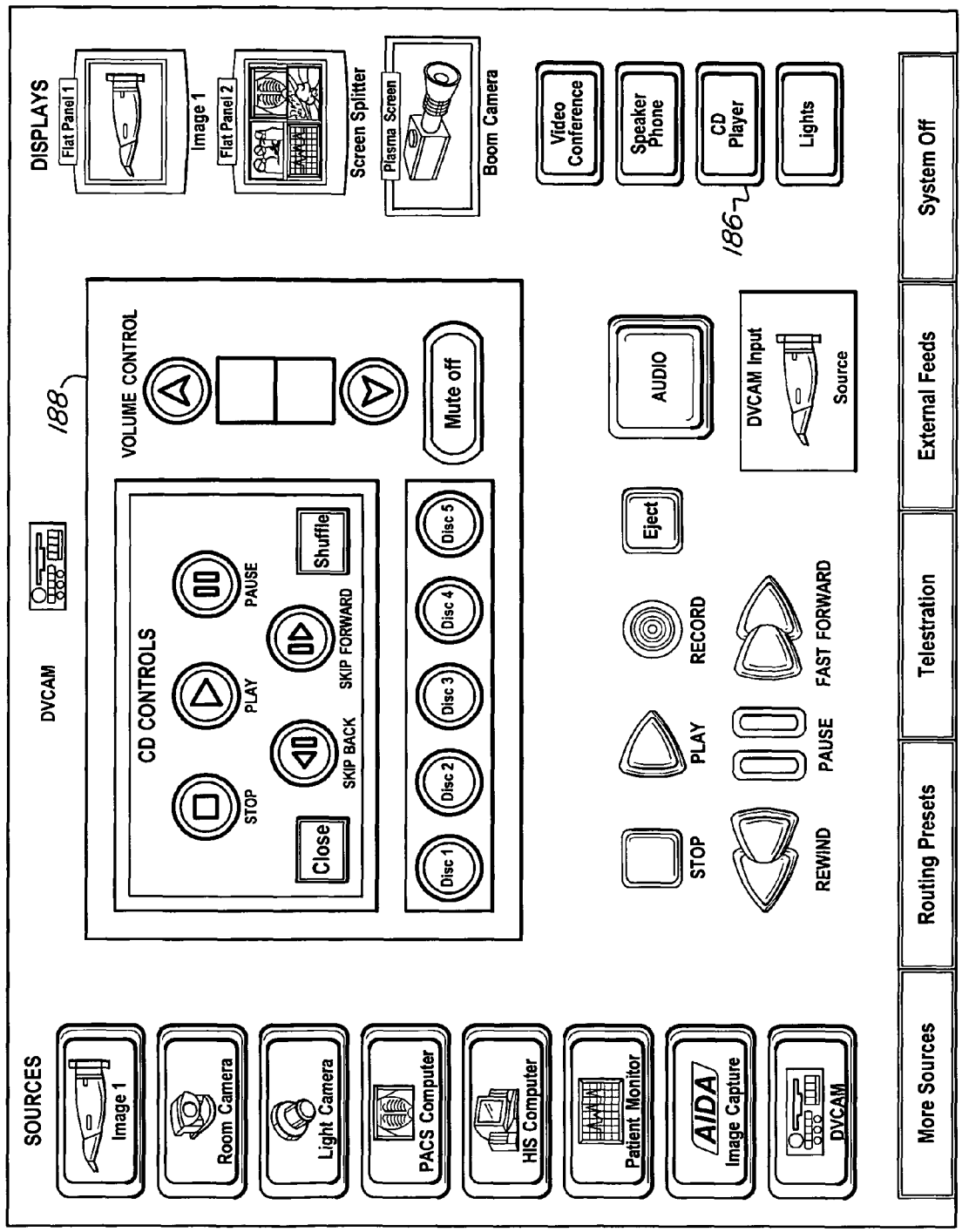
FIG. 20 is a screenshot of the touchscreen of the system of FIG. 1 when a CD icon has been pressed.

Similarly, as illustrated in FIG. 19, the user can press a speakerphone icon 178 to display various controls associated with a speakerphone, such as speed dial buttons 180 for storing phone numbers, a number pad 182 for entering the numbers, and buttons 184 for controlling volume. Likewise, the system may include a CD player and, as illustrated in FIG. 20, the user can press a CD icon 186 for displaying a control panel 188 containing controls associated with the CD player.

Figure 21:
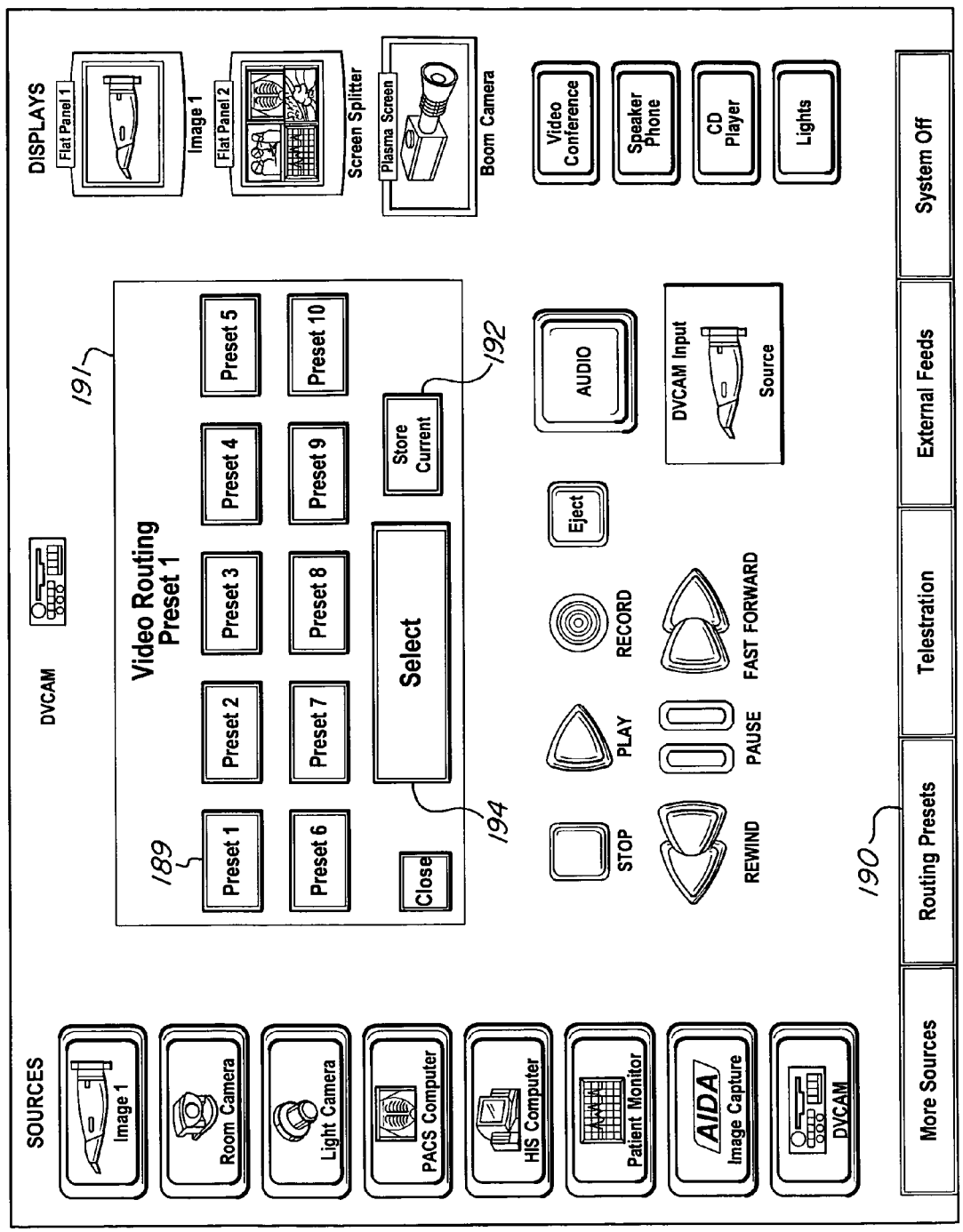
FIG. 21 is a screenshot of the touchscreen of the system of FIG. 1 when a preset icon has been pressed.

If the user desires to save the current setup of the system, the user can press a presets icon 190 located at the bottom of the touchscreen 22 to enter a presets utility. As illustrated in FIG. 21, pressing icon 190 displays a preset window 191 that allows a number of operators of the system to store and name various sets of configurations, which may include the current routing setup for sources and destinations, the light settings, room camera positioning and zoom, and various other configurable items.

Figure 22:
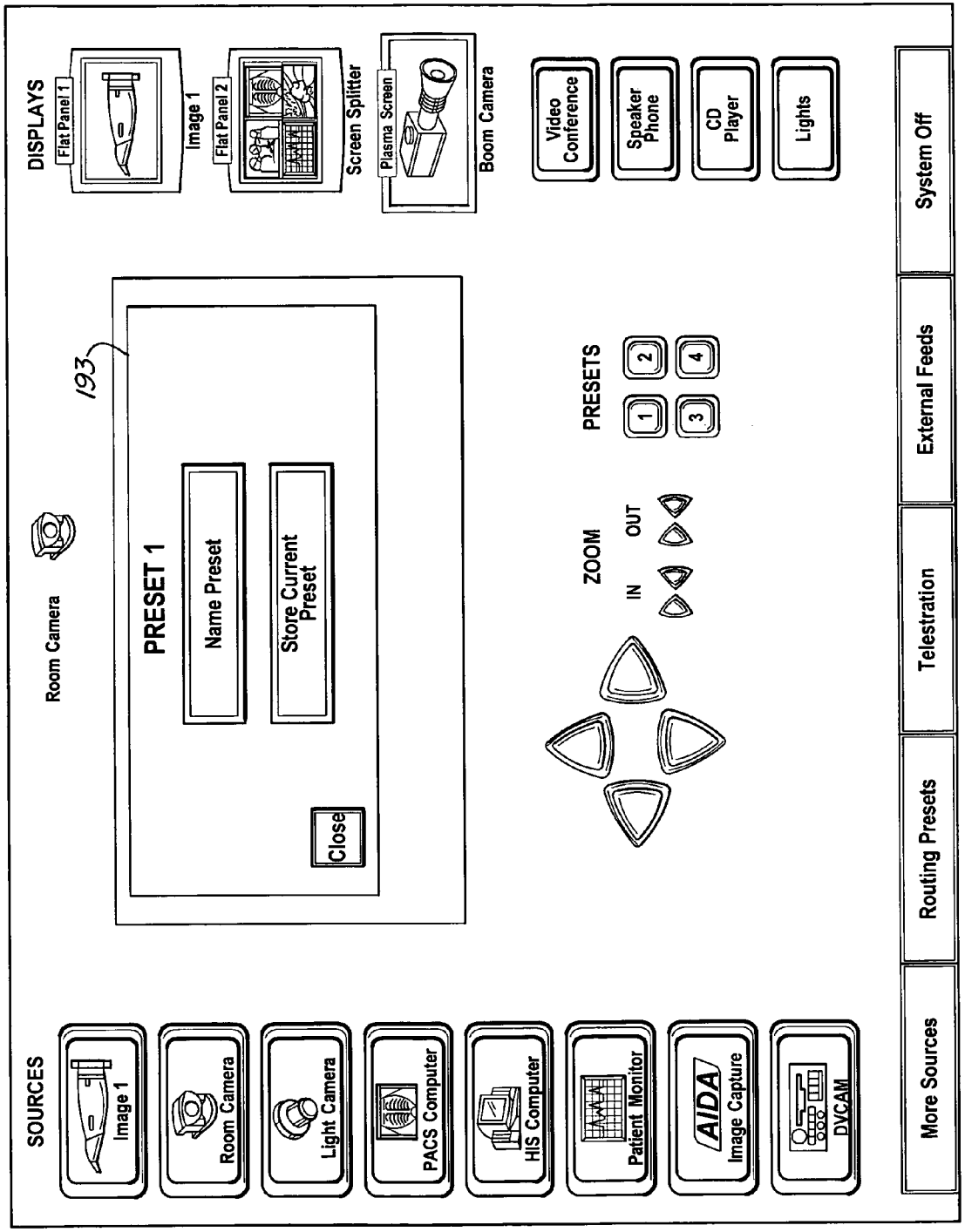
FIG. 22 is a screenshot of the touchscreen of the system of FIG. 1 when a preset store icon has been pressed.

In certain advantageous embodiments, by pressing a store button 192, the user can display a window 193 containing icons for naming and storing the particular set of configurations under a name of his or her choosing, as shown in FIG. 22. At a later time, the user can then automatically set up the system 10 according to this previously stored set of configurations by simply pressing the corresponding preset button 189 and pressing a recall button 194.

Figure 23:
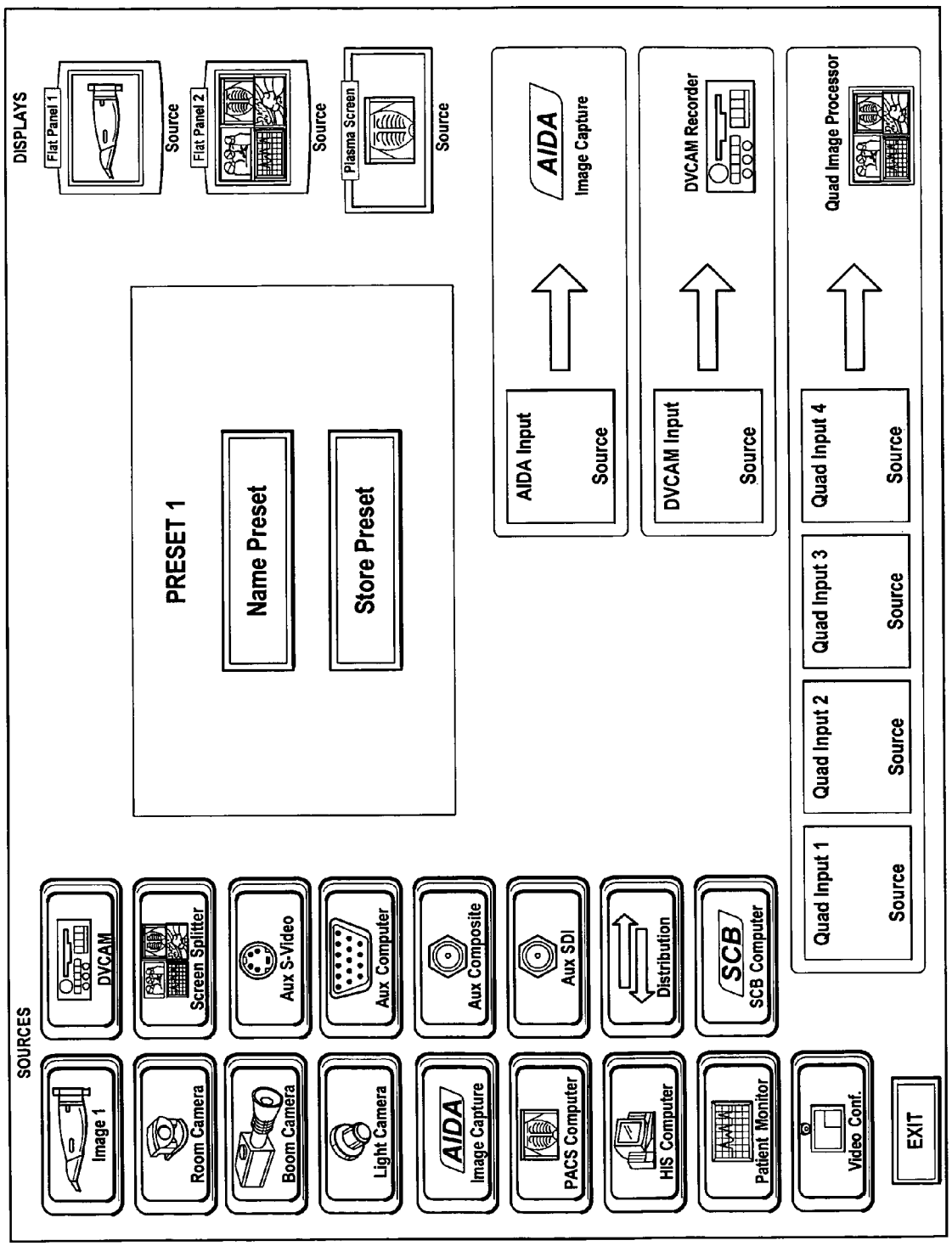
FIG. 23 is a screenshot of the touchscreen of the system of FIG. 1 when a preset overview has been activated.

In other embodiments, the user can display a configurable screen of system 10, such as, for example by continuing to press the preset button 189 for a few seconds. As a result, the user not only receives the window 193 for naming and storing the presets, but the user is also able to first change the configurations of the various devices of the system 10 prior to naming and storing them, as illustrated in FIG. 23.

Figure 24:
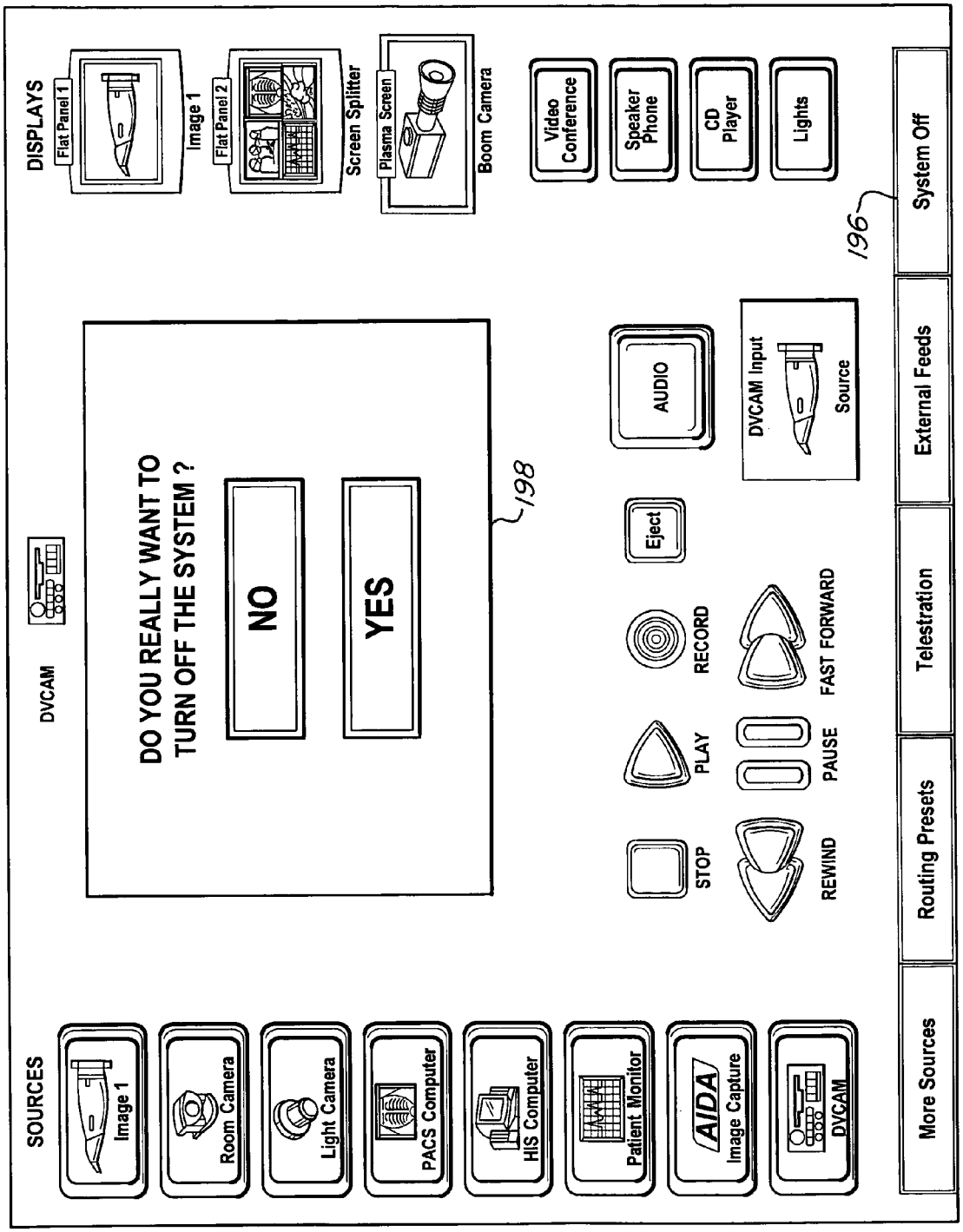
FIG. 24 is a screenshot of the touchscreen of the system of FIG. 1 when a system off icon has been pressed.

When a user decides to exit the system, the user can press a system off icon 196 located at the bottom of the touchscreen 22. As shown in FIG. 24, when the icon 196 is pressed, a query 198 is displayed, which asks the user if they really want to cease use of the system in order to prevent accidental exit therefrom.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A system for controlling the communication of medical imaging data, comprising:
   a computer;
   a plurality of sources of medical imaging data in communication with said computer;
   a plurality of destinations for the medical imaging data in communication with said computer; and
   a touchscreen controlled by said computer for simultaneously displaying a plurality of source icons and a plurality of destination icons;
   wherein the plurality of source icons correspond to said plurality of sources in order to allow a user of said system to select a particular source of medical imaging data, and the plurality of destination icons correspond to said plurality of destinations in order to allow the user to select at least one particular destination to receive the medical imaging data supplied by the selected source.

2. A system as claimed in claim 1, wherein said touchscreen further comprises a display window for displaying medical images generated from the medical imaging data supplied by the selected source.

3. A system as claimed in claim 2, wherein the display window is located between the plurality of source icons and the plurality of destination icons.

4. A system as claimed in claim 2, wherein said touchscreen further comprises a source indicator located adjacent to the display window, wherein the source indicator corresponds to the selected source.

5. A system as claimed in claim 4, wherein the source indicator is located above the display window.

6. A system as claimed in claim 4, wherein the source indicator comprises a graphic corresponding to the selected source.

7. A system as claimed in claim 6, wherein the graphic comprises a graphical representation of the selected source.

8. A system as claimed in claim 6, wherein the graphic comprises a logo designating the selected source.

9. A system as claimed in claim 6, wherein said touchscreen further comprises text describing the selected source adjacent to the source indicator.

10. A system as claimed in claim 2, wherein said touchscreen further comprises a set of controls associated with the selected source.

11. A system as claimed in claim 10, wherein the set of controls is located below the display window.

12. A system as claimed in claim 10, wherein the controls comprise virtual buttons.

13. A system as claimed in claim 12, wherein the controls include panning controls.

14. A system as claimed in claim 12, wherein the controls include zooming controls.

15. A system as claimed in claim 12, wherein the controls include rotating controls.

16. A system as claimed in claim 12, wherein the controls include a freeze control for freezing video.

17. A system as claimed in claim 12, wherein the controls include a save control for saving images.

18. A system as claimed in claim 12, wherein the controls include a control option icon for changing at least some of the controls.

19. A system as claimed in claim 10, wherein:
at least one said plurality of sources of medical imaging data comprises a recording device adapted to receive medical imaging data from another of said sources; and
the set of controls includes a source selection icon to allow a user to display a palette containing the source icons corresponding to the sources of medical imaging data from which the recording device is able to receive medical imaging data and select a source therefrom.

20. A system as claimed in claim 19, wherein the source selection icon includes a source indicator that corresponds to the source from which the recording device is receiving medical imaging data.

21. A system as claimed in claim 2, wherein said touchscreen further includes a telestration icon to allow a user to enter a telestration mode, whereby the user can use a finger to draw on the medical images displayed in the display window.

22. A system as claimed in claim 2, wherein at least one of said plurality of sources of medical imaging data comprises a processor for routing medical imaging data from a plurality of other sources to the computer simultaneously.

23. A system as claimed in claim 22, wherein the display window is divided into a plurality of sections for separately displaying the medical images generated from the medical imaging data supplied by a corresponding plurality of sources when the processor for routing medical imaging data from a plurality of other sources is the selected source.

24. A system as claimed in claim 23, wherein the touchscreen further comprises a set of controls associated with the processor for routing medical imaging data from a plurality of other sources.

25. A system as claimed in claim 24, wherein the set of controls includes a source selection panel having a plurality of sections corresponding to the plurality of sections in the display window to allow a user to select the source from which medical imaging data is used to generate the medical images displayed in the corresponding section of the display window.

26. A system as claimed in claim 25, wherein the set of controls comprises:
mode selectors to allow the user to select one of a plurality of alternate modes; and
any one of a plurality of alternate control panels, the control panel corresponding to the selected mode.

27. A system as claimed in claim 26, wherein one of the alternate control panels comprises a quad image panel.

28. A system as claimed in claim 26, wherein one of the alternate control panels comprises a dual image panel.

29. A system as claimed in claim 26, wherein one of the alternate control panels comprises a picture-in-picture panel.

30. A system as claimed in claim 29, wherein:
the window display includes a first image, and a second image smaller than the first image; and
the control panel includes a size icon for changing the size of the second image.

31. A system as claimed in claim 29, wherein:
the window display includes a first image, and a second image smaller than the first image; and
the control panel includes a position icon for changing the position of the second image.

32. A system as claimed in claim 1, wherein at least one said plurality of sources of medical imaging data comprises a camera.

33. A system as claimed in claim 32, wherein at least one said plurality of sources of medical imaging data comprises an endoscopic camera.

34. A system as claimed in claim 32, wherein at least one said plurality of sources of medical imaging data comprises a room camera.

35. A system as claimed in claim 32, wherein at least one said plurality of sources of medical imaging data comprises a light camera.

36. A system as claimed in claim 32, wherein at least one said plurality of sources of medical imaging data comprises a boom camera.

37. A system as claimed in claim 1, wherein at least one said plurality of sources of medical imaging data comprises a video endoscope.

38. A system as claimed in claim 1, wherein at least one said plurality of sources of medical imaging data comprises a VCR.

39. A system as claimed in claim 1, wherein at least one said plurality of sources of medical imaging data comprises a digital video recorder.

40. A system as claimed in claim 1, wherein at least one said plurality of sources of medical imaging data comprises a device for storing images.

41. A system as claimed in claim 1, wherein at least one said plurality of sources of medical imaging data comprises an image capture device.

42. A system as claimed in claim 1, wherein at least one said plurality of sources of medical imaging data comprises a PACS computer.

43. A system as claimed in claim 1, wherein at least one said plurality of sources of medical imaging data comprises a control computer that centrally controls a plurality of devices.

44. A system as claimed in claim 1, wherein at least one said plurality of sources of medical imaging data comprises a patient monitor.

45. A system as claimed in claim 1, wherein at least one said plurality of sources of medical imaging data comprises a hospital information system.

46. A system as claimed in claim 1, wherein at least one said plurality of sources of medical imaging data comprises an auxiliary input for external devices.

47. A system as claimed in claim 1, wherein at least one said plurality of destinations for the medical imaging data comprises a display.

48. A system as claimed in claim 47, wherein at least one said plurality of destinations for the medical imaging data comprises a flat panel display.

49. A system as claimed in claim 47, wherein at least one said plurality of destinations for the medical imaging data comprises a plasma screen.

50. A system as claimed in claim 47, wherein at least one said plurality of destinations for the medical imaging data comprises a computer monitor.

51. A system as claimed in claim 1, wherein at least one said plurality of destinations for the medical imaging data comprises a recording device.

52. A system as claimed in claim 1, wherein at least one said plurality of destinations for the medical imaging data comprises a storage device.

53. A system as claimed in claim 1, wherein each of the plurality of source icons comprises a virtual button.

54. A system as claimed in claim 53, wherein the virtual button includes a graphic corresponding to the selected source.

55. A system as claimed in claim 54, wherein the graphic comprises a graphical representation of the selected source.

56. A system as claimed in claim 54, wherein the graphic comprises a logo designating the selected source.

57. A system as claimed in claim 1, wherein each of the plurality of destination icons includes a source indicator that corresponds to the selected source for that destination.

58. A system as claimed in claim 1, wherein said touchscreen further comprises an additional sources icon to allow a user to display a palette of additional source icons corresponding to additional sources of medical imaging data and select a source therefrom.

59. A system as claimed in claim 58, wherein the palette of additional source icons is superimposed on the plurality of source icons.

60. A system as claimed in claim 58, wherein the palette of additional source icons disappears after a predetermined period of time.

61. A system as claimed in claim 1, wherein said touchscreen further comprises an external feeds icon to allow the user to display a palette of remote destination icons corresponding to remote destinations to which the medical imaging data can be communicated and select at least one remote destination therefrom.

62. A system as claimed in claim 61, wherein the palette of remote destination icons is superimposed on the plurality of destination icons.

63. A system as claimed in claim 61, wherein the palette of remote destination icons disappears after a predetermined period of time.

64. A system as claimed in claim 63, wherein said touchscreen further comprises a caution indicator if a remote destination has been selected.

65. A system as claimed in claim 64, wherein the caution indicator comprises an additional external feeds icon to allow the user to display the palette of remote destination icons.

66. A system as claimed in claim 64, wherein the caution indicator comprises a blinking light.

67. A system as claimed in claim 61, wherein the palette of remote destination icons includes a termination icon for terminating all communications of medical imaging data to remote devices.

68. A system as claimed in claim 1, wherein said touchscreen further comprises a lighting icon for displaying a palette of lighting controls.

69. A system as claimed in claim 68, wherein the lighting controls include intensity control.

70. A system as claimed in claim 68, wherein the lighting controls include color control.

71. A system as claimed in claim 1, wherein said touchscreen further includes a CD player icon for displaying controls associated with a CD player.

72. A system as claimed in claim 1, wherein said touchscreen further comprises a speakerphone icon for displaying controls associated with a speakerphone.

73. A system as claimed in claim 1, wherein said touchscreen further comprises a videoconference button for displaying a videoconferencing interface.

74. A system as claimed in claim 1, wherein the videoconferencing interface comprises:
 a palette containing the source icons corresponding to the sources of medical imaging data from which the user can select the source of medical imaging data to be communicated to a remote user;
 a display window for displaying medical images generated from the medical imaging data supplied by the selected source;
 a set of controls associated with the selected source; and
 a set of controls associated with videoconferencing.

75. A system as claimed in claim 74, further comprising a control panel containing the set of controls associated with the selected source, said control panel being movable around the videoconferencing interface.

76. A system as claimed in claim 1, wherein said touchscreen further includes a presets icon to allow a user to enter a presets utility.

77. A system as claimed in claim 76, wherein the presets utility includes controls for storing a set of parameters for at least some of the selections of the user and assigning a name to the stored set of parameters.

78. A system as claimed in claim 1, wherein said touchscreen further comprises an off icon for displaying a query to a user to confirm that the user would like to cease use of the system.

79. A system for controlling the communication of medical imaging data, comprising:
 a computer;
 a plurality of sources of medical imaging data in communication with said computer;
 a plurality of destinations for the medical imaging data in communication with said computer;
 a touchscreen controlled by said computer;
 software executing on said computer for displaying on said touchscreen a plurality of source icons corresponding to said plurality of sources of medical imaging data in order to allow a user of said system to select a particular source of medical imaging data; and
 software executing on said computer for displaying on said touchscreen a plurality of destination icons corresponding to said plurality of destinations in order to allow the user to select at least one particular destination to receive the medical imaging data supplied by the selected source.

80. A system as claimed in claim 79, further comprising software executing on said computer for displaying on said touchscreen medical images generated from the medical imaging data supplied by the selected source.

81. A system as claimed in claim 80, wherein the medical images are displayed between the plurality of source icons and the plurality of destination icons.

82. A system as claimed in claim 80, further comprising software executing on said computer for displaying on said touchscreen a source indicator located adjacent to the displayed medical images, wherein the source indicator corresponds to the selected source.

83. A system as claimed in claim 80, further comprising software executing on said computer for displaying on said touchscreen a set of controls associated with the selected source.

84. A system as claimed in claim 83, wherein the set of controls is displayed below the displayed medical images.

* * * * *

Disclaimer

8,069,420 B2 - Roderick Plummer, Corona, CA (US). SYSTEM FOR CONTROLLING THE COMMUNICATION OF MEDICAL IMAGING DATA. Patent dated November 29, 2011. Disclaimer filed November 30, 2015, by the assignee, Karl Storz Endoscopy-America, Inc.

I hereby disclaim the following complete claims 1-2, 4, 6-7, 9-10, 12-14, 17, 22, 32-35, 37, 39-43, 46-48, 50-55, 57, 68, 72-74, 76-77, 79-80, 82 and 82 in said patent.

*(Official Gazette, May 24, 2022)*

(12) INTER PARTES REVIEW CERTIFICATE (572nd)
United States Patent    (10) Number:    US 8,069,420 K1
Plummer    (45) Certificate Issued:    Feb. 12, 2018

(54) SYSTEM FOR CONTROLLING THE COMMUNICATION OF MEDICAL IMAGING DATA

(75) Inventor: Roderick Plummer

(73) Assignee: KARL STORZ ENDOSCOPY-AMERICA, INC.

Trial Numbers:

IPR2015-00677 filed Feb. 18, 2015
    IPR2015-00678 filed Feb. 18, 2015

Inter Partes Review Certificate for:

Patent No.: 8,069,420
    Issued:        Nov. 29, 2011
    Appl. No.:   11/025,715
    Filed:         Dec. 29, 2004

The results of IPR2015-00677 and IPR2015-00678 are reflected in this inter partes review certificate under 35 U.S.C. 318(b).

INTER PARTES REVIEW CERTIFICATE
U.S. Patent 8,069,420 K1
Trial No. IPR2015-00677
Certificate Issued Feb. 12, 2018

AS A RESULT OF THE INTER PARTES REVIEW PROCEEDING, IT HAS BEEN DETERMINED THAT:

Claims 1, 2, 4, 6, 7, 9, 10, 12-14, 17, 22, 32-35, 37, 39-43, 46-48, 50-55, 57, 68, 73, 76, 77, 79, 80, 82 and 83 are cancelled.

\* \* \* \* \*